US010672298B2

(12) United States Patent
Newberry et al.

(10) Patent No.: US 10,672,298 B2
(45) Date of Patent: Jun. 2, 2020

(54) SYSTEM AND METHOD FOR A BLOOD FLOW SIMULATOR

(71) Applicant: Sanmina Corporation, San Jose, CA (US)

(72) Inventors: Robert Newberry, New Hope, AL (US); Matthew Rodencal, Huntsville, AL (US); Nate Roth, Toney, AL (US)

(73) Assignee: SANMINA CORPORATION, San Jose, CA (US)

( * ) Notice: Subject to any disclaimer, the term of this patent is extended or adjusted under 35 U.S.C. 154(b) by 306 days.

(21) Appl. No.: 15/707,914

(22) Filed: Sep. 18, 2017

(65) Prior Publication Data

US 2018/0108275 A1 Apr. 19, 2018

Related U.S. Application Data

(60) Provisional application No. 62/409,271, filed on Oct. 17, 2016.

(51) Int. Cl.
| | |
|---|---|
| *G09B 23/30* | (2006.01) |
| *F03B 13/14* | (2006.01) |
| *A61B 5/02* | (2006.01) |
| *A61B 5/145* | (2006.01) |
| *A61B 5/1495* | (2006.01) |

(52) U.S. Cl.
CPC .............. *G09B 23/303* (2013.01); *A61B 5/02* (2013.01); *A61B 5/145* (2013.01); *A61B 5/1495* (2013.01); *F03B 13/14* (2013.01); *A61B 2560/0223* (2013.01); *Y02E 10/38* (2013.01)

(58) Field of Classification Search
CPC .................................................... G09B 23/303
USPC ............................................................ 434/268
See application file for complete search history.

(56) References Cited

U.S. PATENT DOCUMENTS

| | | | | |
|---|---|---|---|---|
| 2010/0313643 | A1* | 12/2010 | Shyu ........................ | G01D 1/00 |
| | | | | 73/118.01 |
| 2014/0272872 | A1* | 9/2014 | Vozenilek .............. | G09B 23/28 |
| | | | | 434/268 |

OTHER PUBLICATIONS

Ayers, Frederick et al., "Fabrication and characterization of silicone-based tissue phantoms with tunable optical properties in the visible and near infrared domain", Laser Microbeam and Medical Program, Beckman Laser Institute, University of CA, Irvine, 9 pages.

* cited by examiner

*Primary Examiner* — Thomas J Hong
(74) *Attorney, Agent, or Firm* — Loza & Loza, LLP; Julio M. Loza; Jessica W. Smith

(57) ABSTRACT

A blood flow simulator generates a compression and expansion in a test fluid that emulates the pressure waveform created by a heartbeat in blood flow. The blood flow simulator stores a plurality of pressure waveform files that include actual data recorded from a heartbeat, arterial pressure waveform, or venous pressure waveform. One or more of the pressure waveform files may be selected and the pressure waveform file is used by the blood flow simulator 100 to generate a pressure waveform in pressurized fluid. The pressurized fluid flows through a test site, such as a surrogate body part or an optical window or other component with material having similar properties to human tissue. Various target substances may also be added to the fluid in known concentrations for testing and configuration of medical devices at the test site.

19 Claims, 17 Drawing Sheets

SYSTEM AND METHOD FOR A BLOOD FLOW SIMULATOR

CROSS REFERENCE TO RELATED APPLICATIONS

The present application claims priority under 35 U.S.C. § 119(e) to U.S. Provisional Application No. 62/409,271 entitled, "SYSTEM AND METHOD FOR A BLOOD FLOW SIMULATOR," filed Oct. 17, 2016, and hereby expressly incorporated by reference herein.

FIELD

This application relates to a system and method of a simulator system, and in particular to a system and method for a blood flow and blood pressure simulator.

BACKGROUND

Detection of substances and measurement of concentration level or indicators of various substances in a patient's blood vessels is important in health monitoring. One current non-invasive method is known for measuring the oxygen saturation of blood using pulse oximeters. Pulse oximeters detect oxygen saturation of hemoglobin by using, e.g., spectrophotometry to determine spectral absorbencies and determining concentration levels of oxygen. In addition, pulse oximetry may use photoplethysmography (PPG) methods for the assessment of oxygen saturation in pulsatile arterial blood flow based on Beer-Lambert principles. The subject's skin at a 'measurement location' is illuminated with two or more distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood.

Medical devices employing PPG type methods may determine concentration levels of other substances as described in U.S. Utility application Ser. No. 15/275,388 entitled, "System and Method for Health Monitoring using a Non-Invasive, Multi-Band Biosensor," filed Sep. 24, 2016, and hereby expressly incorporated by reference herein. For example, biosensor may detect nitric oxide, liver enzymes, or other substances in blood flow using PPG techniques. PPG circuits may also be used to detect patient vitals such as heart rate, respiration rate, etc.

However, monitoring vitals and substance levels from blood flow in vitro includes many uncontrollable variables. Different substances or physiological reactive mechanisms influence blood-pressure waveforms and PPG measurements of blood substance levels. Thus, it is difficult to control testing conditions and variables in development and calibration of medical devices.

As such, there is a need during development and calibration of medical devices for a simulation system and method for blood flow and blood pressure to test various types of sensors.

SUMMARY

According to a first aspect, a blood flow simulator includes a system controller including a memory for storing a plurality of pressure waveform files and a pressure waveform generator configured to generate a pressure waveform. The blood flow simulator further includes an optical bladder including an optical window test bed, wherein the optical bladder is configured to induce a pressure waveform in fluid in the optical window test bed in response to at least one of the plurality of pressure waveform files.

According to a second aspect, a method for simulating blood flow in a vessel comprises a plurality of pressure waveform files in a memory device of a system controller, wherein the pressure waveform files include data from at least one of: a heart rate, a heartbeat waveform, an arterial blood pressure waveform, a respiration waveform, a background tissue response waveform or a venous blood pressure waveform. The method further comprises receiving a selection of at least one of a plurality of pressure waveform files by the system controller and generating a pressure waveform by a pressure waveform generator in test fluid flowing through a test site in response to the selected one of the plurality of pressure waveform files.

According to a third aspect, a simulator comprises a system controller including a memory for storing a plurality of pressure waveform files, wherein the pressure waveform files include data from at least one of: a heart rate, a heartbeat waveform, an arterial blood pressure waveform, a respiration waveform, a background tissue response waveform, or a venous blood pressure waveform. The simulator further comprises a pressure waveform generator configured to generate a pressure waveform in a gas flowing through an acoustic induction bladder and an optical bladder, wherein the acoustic induction bladder is configured to induce a pressure waveform in fluid in the optical bladder in response to the pressure waveform in the gas flowing through the acoustic induction bladder.

According to one or more of the above aspects, the optical window test bed comprises a material with elasticity and optical properties that are similar to human tissue.

According to one or more of the above aspects, the pressure waveform generator comprises a pressure bladder configured to hold the gas, an amplifier for amplifying data from at least one of the plurality of pressure waveforms to generate an amplified data signal, and a pressure inducer configured to compress the pressure bladder in response to the amplified signal to generate the pressure waveform in the gas. The pressure waveform generator further comprises at least one actuator configured to exert pressure on the pressure inducer in response to the amplified signal.

According to one or more of the above aspects, an injection valve is configured for injecting a target substance into the fluid to obtain a known concentration of the target substance in the fluid.

DETAILED DESCRIPTION

Figure 1:
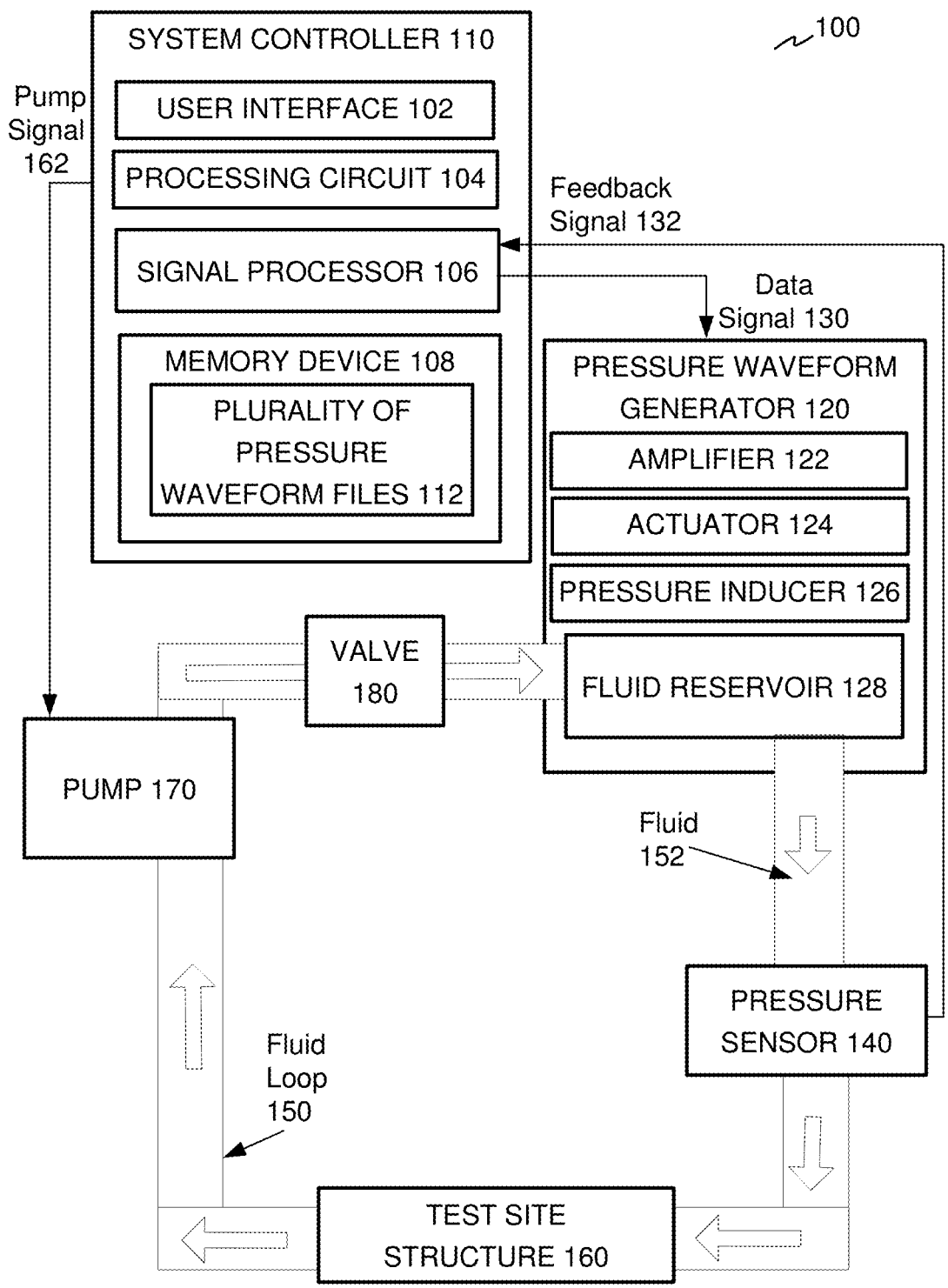
FIG. 1 illustrates a schematic block diagram of an embodiment of an exemplary blood flow simulator.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview

A blood flow simulator produces fluid compression in a fluid loop that emulates the pressure waves in a blood vessel. For example, pressure waves in a blood vessel are created by the heartbeat and respiration. The blood flow simulator generates a pressure waveform in response to a selected pressure waveform file. The pressure waveform file may include data derived from a heart rate, respiration rate, arterial or venous pressure waveforms. The pressure waveform file is processed to generate a data signal. The data signal is amplified (and converted from digital to analog or other processing performed) and the amplified data signal drives a pressure waveform generator to compress fluid in the fluid loop.

For example, the pressure waveform generator may include a pressure inducer that is coupled to an electromagnetic or piezoelectric actuator. The pressure inducer applies a force to compress the fluid loop to generate a pressure waveform in the fluid. The pressure waveform emulates a pulse or pressure conditions in the fluid loop as that created by a heartbeat in a blood vessel, such as in arteries or veins. The pressurized fluid may flow through a simulated body part, such as a finger, toe, arm, leg, etc. The generated pressure waveform then induces a change of fluid volume in the simulated body part via hydraulic action, much the same way that a heartbeat induces a volumetric change in the arteries due to hydraulic action and the elastic nature of blood vessels. Thus, the pressure waveform generator changes the blood volume of the "simulated arteries" (e.g., the section of the fluid loop) in the simulated body part.

The blood flow simulator is configured with multiple settings to adjust the pressure applied by the pressure inducer to simulate various types of heartbeats. For example, the pressure waveform generated by the electromagnetic or piezoelectric actuator may be adjusted to represent a heartbeat of a high blood pressure patient, a patient in cardiac arrest, a normal patient, or a patient suffering from any number of heart conditions or irregularities.

In addition, a predetermined concentration level of a substance may be added or included in the fluid in the fluid loop. The known concentration level of the substance assists in the development and calibration of a biometric sensor for detecting concentration levels of substances in blood. For example, the blood flow simulator may be used for testing and calibrating medical devices such as pulse oximeters or PPG sensors. The substance may include a liquid, gas, solid, a solid-liquid solution, a liquid solution with dissolved gasses, a solid liquid solution with dissolved gasses, a biological structure, or a number of biological structures.

Embodiment-Blood Flow Simulator

FIG. 1 illustrates a schematic block diagram of an embodiment of an exemplary blood flow simulator 100. The blood flow simulator 100 includes a system controller 110 with one or more processing circuits and a memory device 108. In one aspect, the memory device 108 may include one or more non-transitory processor readable memories that store instructions which when executed by the processing circuit, causes the processing circuit to perform one or more functions described herein. The memory device 108 may also store a plurality of pressure waveform files 112 used to control a pressure waveform generator 120 as described in more detail herein. The system controller 110 may also include a user interface, such as a display, touch screen, keyboard, mouse, etc., and a signal processor 106. The signal processor 106 is configured to perform processing on data from a selected pressure waveform file 112 to generate a data signal 130. The signal processor 106 may receive a feedback signal from one or more pressure sensors 140 that obtain pressure readings of fluid 152 in the fluid loop 150 as described in more detail herein.

The blood flow simulator 100 further includes a pump 170 and a test site structure 160 (such as an optical window or simulated body part) interconnected by the fluid loop 150. The pump may include a peristaltic or other type of pump. The pump 170 is configured to pressurize the fluid loop 150 to an initial pressure. The pump 170 is a type of positive displacement pump. The fluid 152 is contained within a flexible tube fitted inside a circular pump casing of the pump 170. A rotor with a number of "rollers", "shoes", "wipers", or "lobes" attached to the external circumference of the rotor compresses the flexible tube. As the rotor turns, the part of the tube under compression is pinched closed (or "occludes") thus forcing the fluid to move through the tube. Additionally, as the tube opens to its natural state after the passing of the cam ("restitution" or "resilience") fluid flow is induced to the pump 170. The pump 170 pressurizes the fluid 152 through the fluid loop 150 in response to a pump signal 162 from the system controller 110. For example, the user interface 102 of the system controller 110 may include one or more settings for an initial pressure and/or a fluid flow rate. A user may adjust operation of the pump 170, such as initial pressure and fluid flow rate, through the user interface 102. The system controller 110 controls the settings (on/off/rate) of the pump 170 in response to user input. Though a pump 170 is described herein, other type of pumps may also be implemented.

To generate a simulated pulse waveform, one of a plurality of pressure waveform files 112 is selected from the memory device 108 of the system controller 110 through the user interface 102. The pressure waveform files 112 include data that may be simulated or may be recorded from actual patients. For example, the pressure waveform files 112 may include data from recordings of actual patients or simulations of pressure waveforms indicative of various types of heartbeats, including normal and abnormal heart rates and normal and abnormal cardiac rhythms. The pressure waveform files 112 may include data for simulating arrhythmia, such as an abnormally slow or fast heart rate or an irregular cardiac rhythm. The pressure waveform files indicative of arrhythmia may include data for an accelerated heart rate, a low heart rate, a high blood pressure patient, a patient in cardiac arrest, a patient with arterial fibrillation or a patient with other heart defects or heart conditions.

One or more of the pressure waveform files may also include background tissue response waveforms. The background tissue response waveform includes a nominal DC response of an optical sensor, e.g. PPG circuit response. The background tissue response waveform varies depending on the underlying tissue type in tests on actual patients. The pressure waveform files 112 may include different background tissue response waveforms to simulate different tissue types. The plurality of pressure waveform files 112 may thus include data from at least one of: a heart rate, a heartbeat waveform, a respiration rate, a background tissue response waveform, arterial pressure waveform, or venous pressure waveform.

One of the plurality of pressure waveform files 112 is selected by a user through the user interface 102. The system controller 110 may perform data signal processing to generate an output data signal from the selected pressure waveform file 112. The system controller 110 transmits the data signal 130 to the pressure waveform generator 120. The pressure waveform generator 120 is configured to induce the pressure waveform in the fluid 152 in the fluid loop 150.

In one embodiment, the pressure waveform generator 120 includes an amplifier 122, a pressure actuator 124 and a pressure inducer 126. In use, the amplifier 122 first amplifies the data signal 130 (and converts the data signal 130 from digital to analog or performs other signal processing) to generate an amplified data signal. The amplified data signal is used to drive the pressure actuator 124.

In one aspect, the pressure actuator 124 includes an electromagnetic actuator such as an acoustic speaker coupled to the pressure inducer 126. The amplified data signal drives the one or more actuators 124 in parallel. The one or more actuators 124 generate a force that pushes the pressure inducer 126 against an elastic or malleable fluid reservoir 128 in response to the amplified data signal. The pressure inducer 126 may include a plate, block, cylinder, piston or other one or more components configured to exert pressure exert the fluid reservoir 128. The fluid reservoir 128 is coupled to the fluid loop 150. The connection from the pump 170 to the fluid reservoir 128 may contain a one-way valve 180, or similar mechanism to prevent fluid flow back towards the pump 170. The one-way valve 180 thus keeps the fluid 152 with the induced pressure waveform flowing towards the test site structure 160.

The pressure inducer 126 is configured to compress the fluid reservoir 128 against a ridged structure that conforms closely to the shape of the fluid reservoir 128, herein referred to as the reservoir containment. The compression of the fluid reservoir 128 between the pressure inducer 126 and the reservoir containment creates a pressure waveform in the fluid loop 150 via hydraulic forces.

In another aspect, the pressure actuator 124 includes one or more piezoelectric elements connected to the pressure inducer 126. When the amplified data signal is transmitted through the piezoelectric elements, it creates a mechanical motion that pushes the pressure inducer 126 against the elastic or malleable fluid reservoir 128.

The pressurized fluid flows from the pressure waveform generator 120 through a test site structure 160. The test site structure 160 may include a simulated body part, such as a finger, toe, ear lobe, arm, leg, etc. The test site structure 160 may alternatively include a piece of tubing or fluid reservoir comprising a material with comparable or approximately similar optical properties and elasticity as skin or tissue. A medical device or sensor may then perform one or more measurements on the test site structure 160.

One or more pressure sensors 140 may be included to measure the pressure in the fluid loop 150. The pressure sensor provides a feedback signal 132 to the signal processor 106 in the system controller 110. The signal processor 106 may use a linear or non-linear closed loop filter or control loop to compensate for and correct distortions in the output pressure wave based on the feedback signal 132. The signal processor 106 may also use an open loop filter to compensate for and correct distortions in the output pressure wave.

The blood flow simulator 100 thus produces a rhythmic fluid compression and expansion that emulates the pressure waveform created by a heartbeat in arterial or venous blood flow. The pressure waveform files include actual data recorded from a heartbeat, arterial pressure waveform, or venous pressure waveform. The pressure waveforms in the blood flow simulator 100 thus emulate a pulse or pressure conditions in blood vessels. The pressure conditions for arrhythmia, such as an abnormally slow or fast heart rate or an irregular cardiac rhythm, may also be induced by the blood flow simulator 100. The pressurized fluid flows through a test site structure 160, such as a surrogate body part or an optical window or other component with material having approximately similar elasticity and/or optical properties to human tissue. Various target substances may also be added to the fluid in known concentrations for testing and configuration of medical devices at the test site.

Embodiment-Pressure Waveform Generator

Figure 2A:
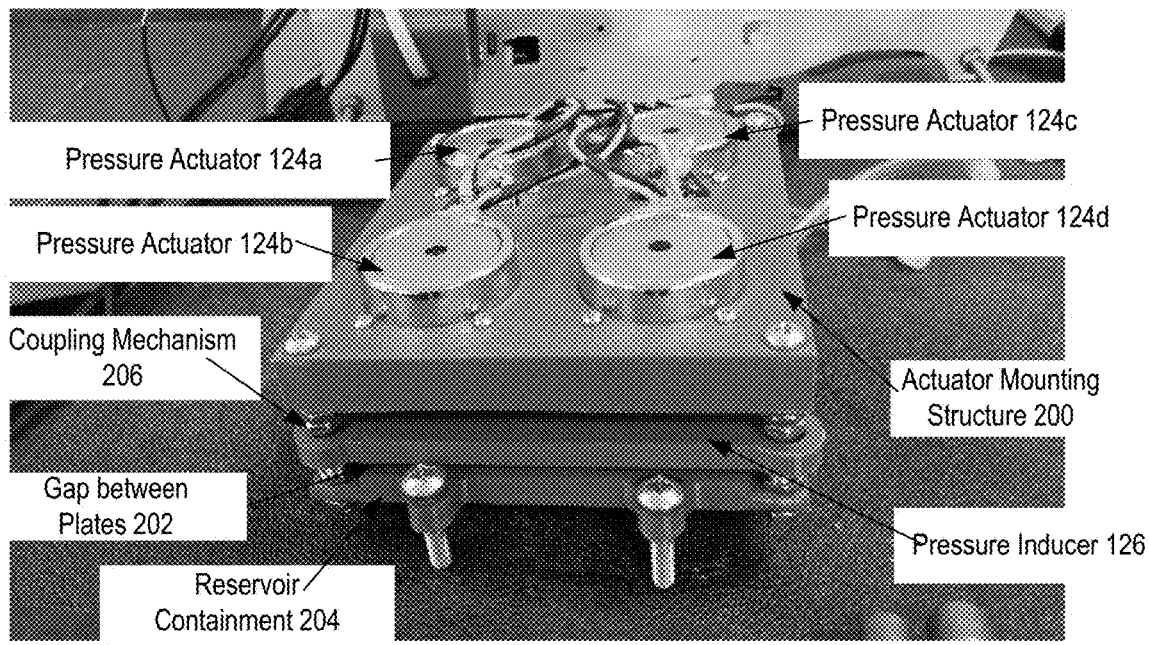
FIG. 2A illustrates a perspective view of an embodiment of an exemplary pressure waveform generator.

FIG. 2A illustrates a perspective view of an embodiment of an exemplary pressure waveform generator 120. In one aspect, the pressure waveform generator 120 includes one or more piezoelectric or electromagnetic actuators. The piezoelectric or electromagnetic actuators are mounted to a ridged structure, herein referred to as an actuator mounting structure 200. The amplifier 122 amplifies the data signal 130, and the piezoelectric elements or electromagnetic coils generate a force against the pressure inducer 126. This force pushes the pressure inducer 126 against an elastic or malleable fluid reservoir 128. The fluid reservoir 128 is connected to the fluid loop 150.

The connection from the pump 170 to the fluid reservoir 128 may contain a one-way valve 180, or another mechanism to provide for fluid flow in one direction. The one-way valve 180 prevents the fluid 152 from flowing in the fluid loop 150 backwards from the fluid reservoir 128 back towards the pump 170. The one-way valve 180 thus keeps the fluid 152 with the induced pressure wave flowing towards the test site structure 160.

Figure 2B:
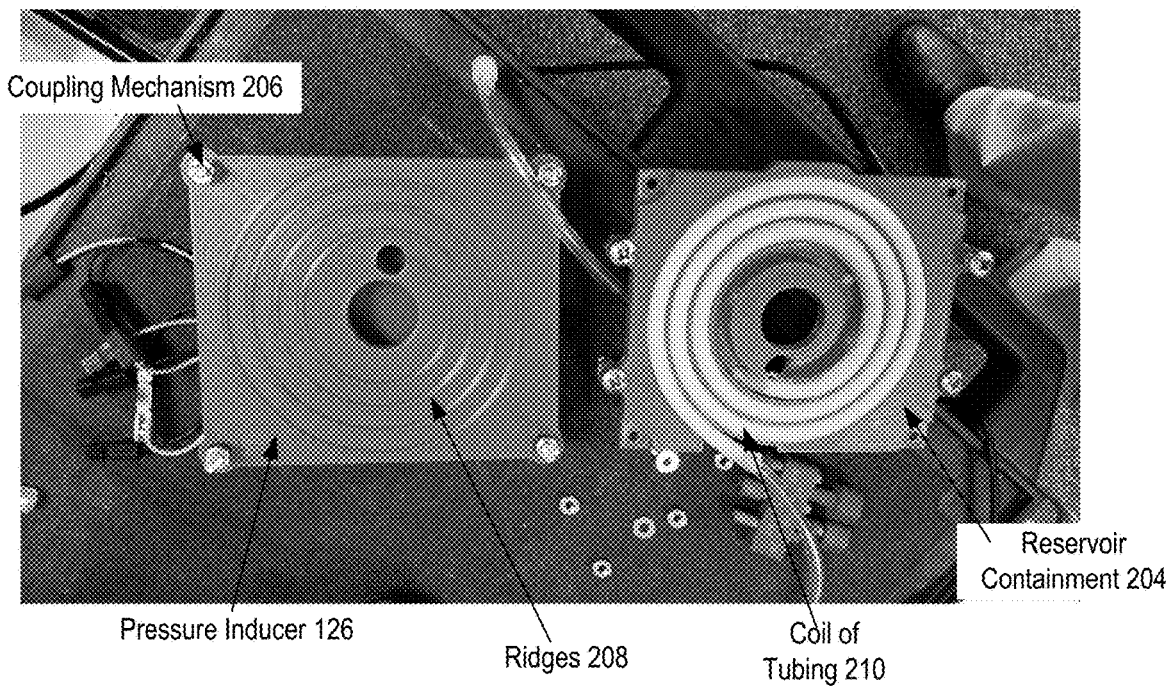
FIG. 2B illustrates a perspective view of an embodiment of an exemplary pressure inducer.

FIG. 2B illustrates a perspective view of an embodiment of an exemplary pressure inducer 126. In one aspect, the fluid reservoir 128 includes a coil of latex tubing 210, herein referred to as the compression coil. The fluid reservoir 128 includes a coil of latex tubing 210 partially contained by the reservoir containment 204 in such a way where the tubing is sandwiched between the pressure inducer 126 and the reservoir containment walls. The length and width of the coil of latex tubing 210 and the geometry of the pressure inducer 126 and reservoir containment 204 are determined to provide a sufficient surface area of the coil of tubing 210 against the pressure inducer to distribute the pressure wave through the fluid 152.

For example, by applying the amplified signal to the piezoelectric material, the pressure inducer 126 will compress the coil of tubing 210 against the reservoir containment 204. The compression of the coil of the tubing 210 then induces the pressure wave in the reservoir 128 corresponding to the amplified signal. This pressure wave creates pressure conditions in the fluid loop 150 as that created by the recorded pressure waveform. The pressure waveform files 112 may thus be used to generate various systolic and diastolic pressures and waveforms that emulate various pressure waveforms in a blood vessel. These pressure waves create pressure conditions in the fluid that are similar or approximately the same as to ones created by a heartbeat in a blood vessel. The system is thus capable of generating various systolic and diastolic pressures and waveforms that emulate blood being pumped through blood vessels, e.g. arterial blood flow.

In an embodiment, a gap or distance between the reservoir containment 204 and the pressure inducer 126 is determined to provide at least a minimum threshold of compression of the fluid reservoir 128. The gap 202 between the plates needs to be sufficient such that the compression generates the desired volume change or displacement of the fluid 152 in the fluid loop 150. For example, the pressure inducer 126 may only have a short range of motion in response to the actuators 124. A coupling mechanism 206 may be used to secure the reservoir containment 204 to the the pressure inducer 126. The coupling mechanism may include one or more bolts and nuts. The width or number of nuts may be adjusted to adjust the gap 202 between the plates.

The pressure inducer 126 may include ridges 208 or other structure to surround and compress the coil of tubing 210 when the pressure inducer 126 is in the neutral or unloaded position. The pressure inducer 126 then further compresses the reservoir 128 in response to the pressure actuators 124 to displace the fluid 152 in the reservoir 128 to generate a pressure waveform. The pressure inducer 126 may apply a uniform pressure across the pressure inducer 126. In another aspect, the pressure actuator 124 may apply a non-uniform pressure across the pressure inducer 126. In another aspect, the pressure inducer 126 may be mechanically secured through a hinge to the reservoir containment 204 in one axis.

Figure 3:
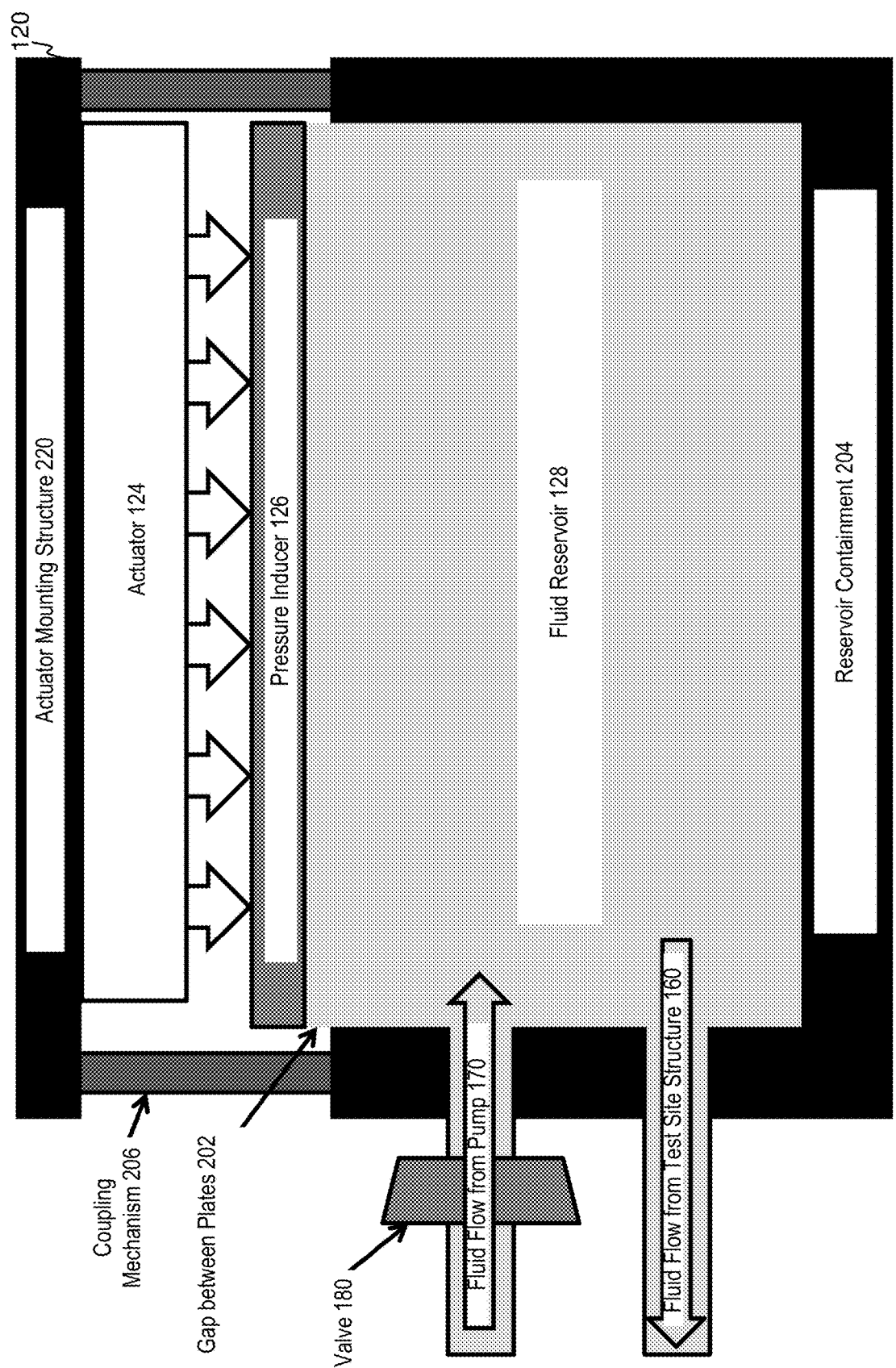
FIG. 3 illustrates a schematic block diagram of an embodiment of an exemplary pressure waveform generator wherein the pressure inducer applies a uniform pressure across the pressure inducer.

FIG. 3 illustrates a schematic block diagram of an embodiment of an exemplary pressure waveform generator 120 wherein the pressure inducer 126 applies a uniform pressure across the pressure inducer 126. In this embodiment, the one or more actuators 124 apply an approximately uniform force on the surface area of the pressure inducer 126. An amplifier 122 amplifies the data signal 130, and the actuator 124 generates a linear force against the pressure inducer 126. This force uniformly pushes the pressure inducer 126 against the elastic or malleable reservoir 128. A gap 202 or distance between the reservoir containment 204 and the pressure inducer 126 is determined to provide at least a minimum threshold of compression of the fluid reservoir 128. The gap 202 between the plates needs to be sufficient so that the compression generates the desired volume change or displacement of the fluid 152 in the fluid loop 150 in the test site structure 160.

The fluid reservoir 128 is connected to the fluid loop 150. The connection from the pump 170 to the fluid reservoir 128 includes the one-way valve 180 to prevent the fluid 152 from flowing in the fluid loop 150 backwards from the fluid reservoir 128 back towards the pump 170. The fluid reservoir 128 is mechanically coupled or situated adjacent to the reservoir containment 204. The compression of the fluid reservoir 128 between the pressure inducer 126 and the reservoir containment 204 creates a pressure wave in the fluid loop 150 via hydraulic forces. The pressure inducer 126 is coupled to the piezoelectric or electromagnetic actuator 124 but is allowed to move freely against the fluid reservoir 128 when pushed by the one or more actuators 124. The reservoir containment 204 and pressure inducer 126 are attached by a coupling mechanism 206 that mechanically couples or otherwise secures the plates. In one embodiment, the coupling mechanism includes bolts and nuts at the corners of the plates.

Figure 4:
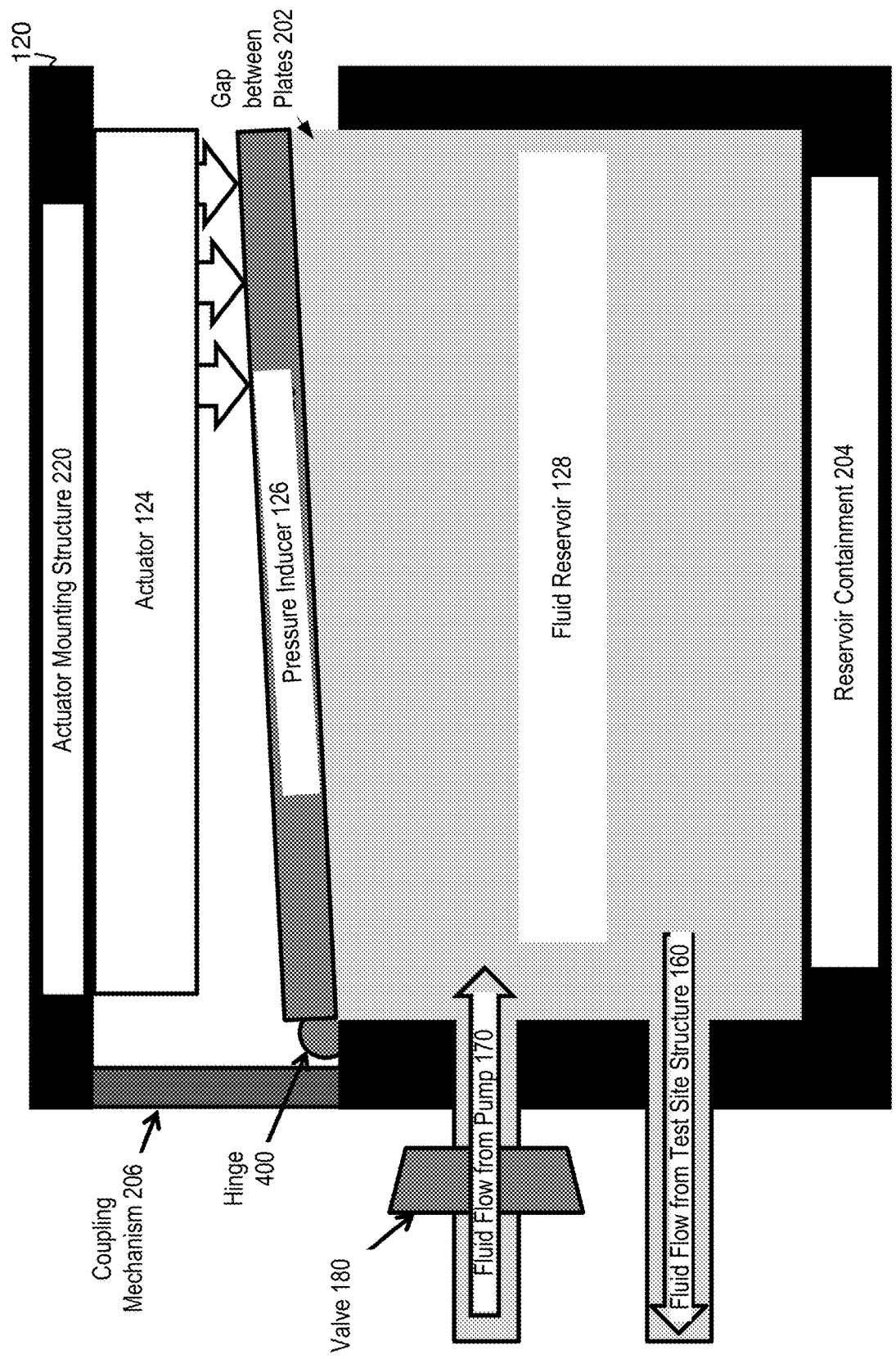
FIG. 4 illustrates a schematic block diagram of an embodiment of an exemplary pressure waveform generator wherein the pressure inducer applies a non-uniform pressure across the pressure inducer.

FIG. 4 illustrates a schematic block diagram of an embodiment of an exemplary pressure waveform generator 120 wherein the pressure inducer 126 applies a non-uniform pressure across the pressure inducer 126. In this embodiment, the pressure inducer 126 is coupled or secured to the reservoir containment 204 by a hinge 400 at a first side. The piezoelectric or electromagnetic actuators 124 apply a force on the surface area near an opposite side of the pressure inducer 126. The linear force on the opposite side of the pressure inducer 126 forces the pressure inducer 126 to rotate around the hinge 400. The pressure inducer 126 thus generates a force against the fluid reservoir 128. A gap 202 or distance between the reservoir containment 204 and the opposite side of the pressure inducer 126 is determined to provide at least a minimum threshold of compression of the fluid reservoir 128. The distance needs to be sufficient such that the compression generates the desired volume change or displacement of the fluid 152 in the fluid loop 150 in the test site structure 160.

The fluid reservoir 128 is connected to the fluid loop 150. The connection from the pump 170 to the fluid reservoir 128 may include the one-way valve 180 to prevent the fluid 152 from flowing in the fluid loop 150 backwards from the fluid reservoir 128 back towards the pump 170. The fluid reservoir 128 is mechanically attached to the reservoir containment 204. The compression of the fluid reservoir 128 between the pressure inducer 126 and the reservoir containment 204 creates a pressure wave in the fluid loop 150 via hydraulic forces. The pressure inducer 126 is attached to the reservoir containment 204 to move about the hinge 400 against the fluid reservoir 128 when pushed by the one or more actuators 124. The reservoir containment 204 is coupled by a coupling mechanism 206, e.g. bolts and nuts at the corners of the plates.

Second Embodiment—Blood Flow Simulator

Figure 5:
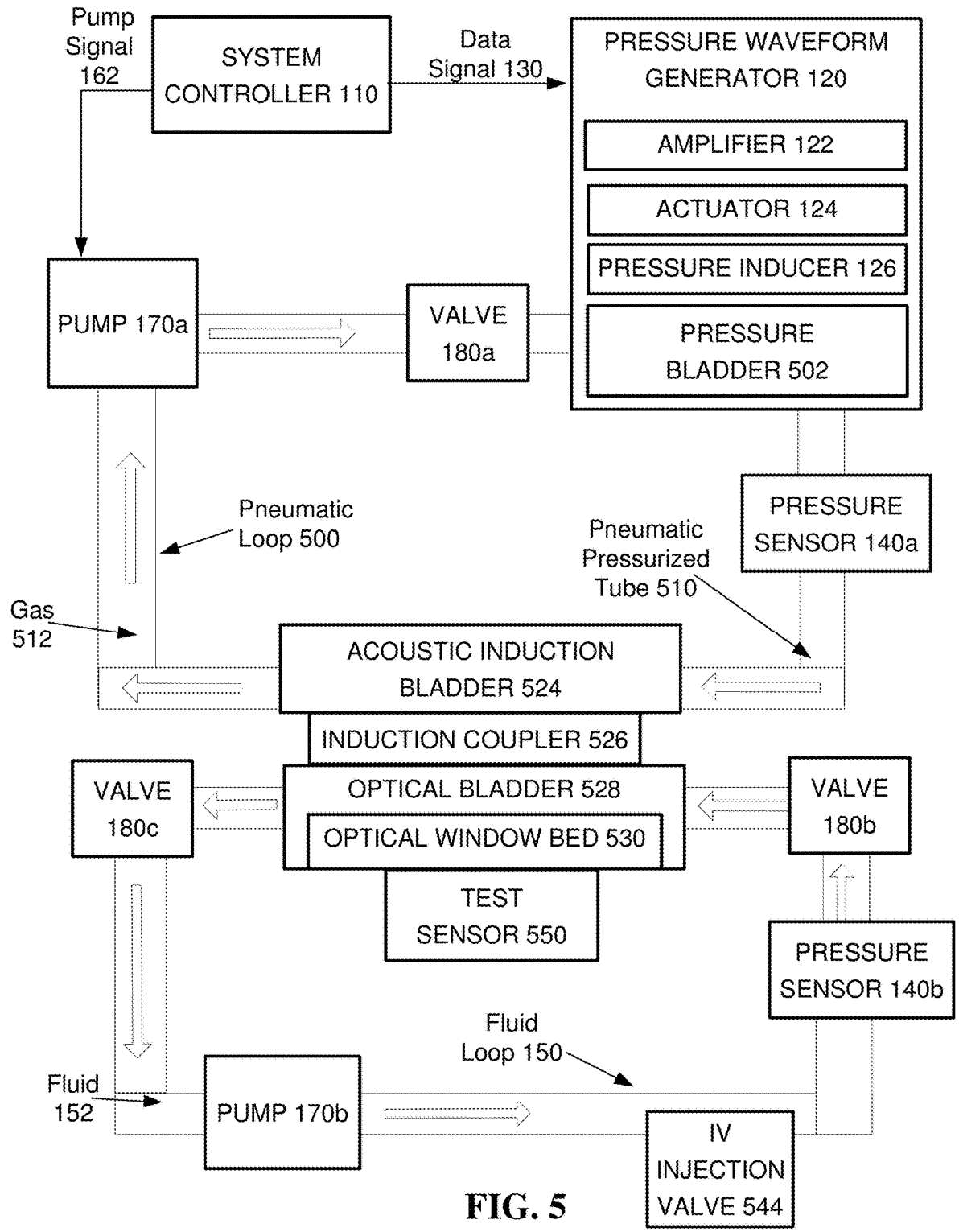
FIG. 5 illustrates a schematic block diagram of another embodiment of a blood flow simulator.

FIG. 5 illustrates a schematic block diagram of another embodiment of a blood flow simulator 100. In this embodiment, the blood flow simulator 100 includes a pneumatic loop 500 and fluid loop 150. The pneumatic loop is configured to induce a pressure waveform onto an optical bladder in the fluid loop 150.

The pneumatic loop 500 includes a first pump 170a, a pressure waveform generator 120 and at least a first pressure sensor 140a. The pump 170a pressurizes a gas 512 through a pneumatic pressurized tube 510 from the pressure waveform generator 120 to an acoustic induction bladder 524. The gas 512 may include a single gas, such as oxygen, or include a mixture of gases, such as air.

The pressure waveform generator 120 includes a pressure actuator 124 coupled to a pressure inducer 126. The pressure inducer 126 is configured to exert a force against a pressure bladder 502. The actuator 124 creates a mechanical motion which generates a force that pushes the pressure inducer 126 against the pressure bladder 502. The pressure bladder 502 includes, e.g., an elastic or malleable balloon configured to hold pressurized air or other gas 512. The pressure inducer 126 creates a pressure waveform in the gas 512 in the pressure bladder 502.

The pressurized gas 512 from the pressure bladder 502 flows through a pneumatic pressurized tube 510 to an acoustic induction bladder 524. The acoustic induction bladder 524 includes, e.g. an elastic or malleable balloon. The acoustic induction bladder 524 increases and decreases in volume in response to the pressure wave in the gas 512.

The acoustic induction bladder 524 is coupled to an induction coupler 526. The induction coupler 526 includes a pressure inducer or other nonflexible component. The acoustic induction bladder 524 exerts pressure against the induction coupler 526 in response to the pressure waveform as it increases and decreases in volume. In response, the induction coupler 526 exerts a similar pressure wave against an optical bladder 528. The induction coupler 526 thus exerts pressure against the optical bladder 528 in response to the pressure waveform.

The optical bladder 528 is included in the fluid loop 150. The fluid loop 150 includes a second pump 170b configured to pressurize or pump fluid 152 through the fluid loop 150. The first pump 170a and the second pump 170b may include peristaltic pumps or other types of pumps. The optical bladder 528 is coupled to the fluid loop 150. The connection from the pump 170b to the optical bladder 528 may include a one-way valve 180b, or similar mechanism to prevent fluid flow back towards the pump 170b. Another one way valve 180c may also be included coupled to an output of the optical bladder 528. The one-way valves 180b and 18c may thus keep the fluid 152 with the induced pressure wave flowing towards or within the optical bladder 528.

One or more pressure sensors 140b may be included to measure the pressure in the fluid loop 150. The one or more pressure sensors 140b provide a feedback signal 132 to the signal processor 106 in the system controller 110.

In an embodiment, the optical bladder 528 includes an optical window bed 530. The optical window bed 530 may comprise material with approximately similar optical properties as tissue. The optical window bed 530 thus provides a simulated tissue site for testing a test sensor 550, such as a PPG sensor, heart rate sensor, respiration sensor, pulse oximeter, etc.

The separation of the fluid loop 150 from the pressure waveform generator 120 has several advantages. For example, the fluid 152 and surfaces touching the fluid 152 are more isolated from other components of the blood flow simulator 100. The fluid 152 is thus less likely to be contaminated. The optical bladder 528 also may have an improved dynamic response to the acoustic induction bladder 524. For example, the AC component of the pressure wave in the optical bladder 528 is more responsive in this embodiment.

In addition, since the fluid loop 150 is a closed fluid loop, the fluid 152 may be used to simulate blood arterial flow by introducing known concentrations of substances. For example, after the fluid loop 150 is pressurized within the blood flow simulator 100, then a known concentration of a substance may be injected into the fluid 152, e.g. through an IV injection valve 544 into the fluid loop 150. The known substance may include bacteria, enzymes, pharmaceuticals or other substances which can then be tested and analyzed for detection using a test sensor 550. For example, a PPG type sensor may be tested to measure a sensitivity and accuracy to those injected substances and for configuration of the PPG type sensor. This testing can be very useful for pharmaceutical sensor applications in detecting precise dosing amounts in arterial blood non-invasively during drug delivery. Dissolved gases may also be introduced to the fluid 152 in a similar manner to measure the effects of dosing medical gases into the blood stream, e.g. in order to test a PPG sensor's sensitivity to those substances. For example, nitric oxide (NO) or oxygen may be included to test oxygen saturation levels or NO levels.

Though an actuator, pressure inducer and pressure bladder are described herein, other components and methods may be implemented to induce the pressure waveform in the pneumatic loop 500. For example, a hydraulic or pneumatic piston may be implemented to induce the pressure waveform in the pneumatic loop 500.

Figure 6A:
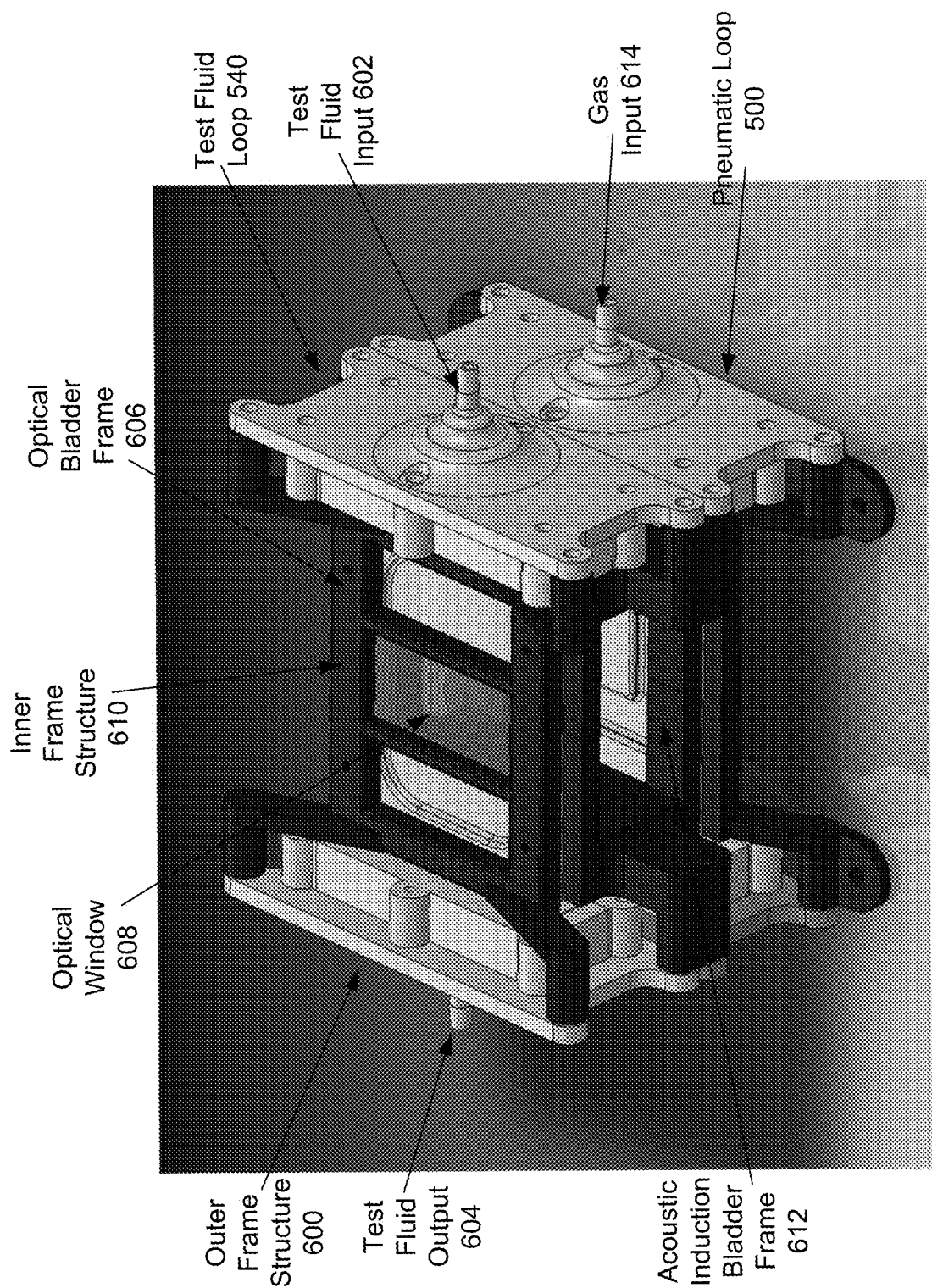
FIG. 6A illustrates an elevational view of an embodiment of the blood flow simulator with a pneumatic loop and a fluid loop.

FIG. 6A illustrates an elevational view of an embodiment of the blood flow simulator 100 with a pneumatic loop 500 and fluid loop 150. In one aspect, the blood flow simulator 100 includes an outer frame structure 600 and an inner frame structure 610. The outer frame structure 600 provides support for input and output connections to the fluid loop 150 and the pneumatic loop 500. For example, the outer frame structure 600a includes a test fluid input 602 for receiving fluid 152 into the optical bladder 528, and a test fluid output 604 for the drainage or outflow of the fluid 152 from the optical bladder 528. The outer frame structure 600 further includes a gas input 614 for receiving gas 512 from the pneumatic pressurized tube 510. The gas 512 flows into the acoustic induction bladder 524 and flows to a gas output (not shown).

The inner frame structure 610 includes an optical bladder frame 606 that supports the optical bladder 528. An optical window 608 including a transparent window or opening is situated over the optical window bed 530 of the optical bladder 528. The inner frame structure 610 further includes an acoustic induction bladder frame 612 that supports the acoustic induction bladder 524.

Figure 6B:
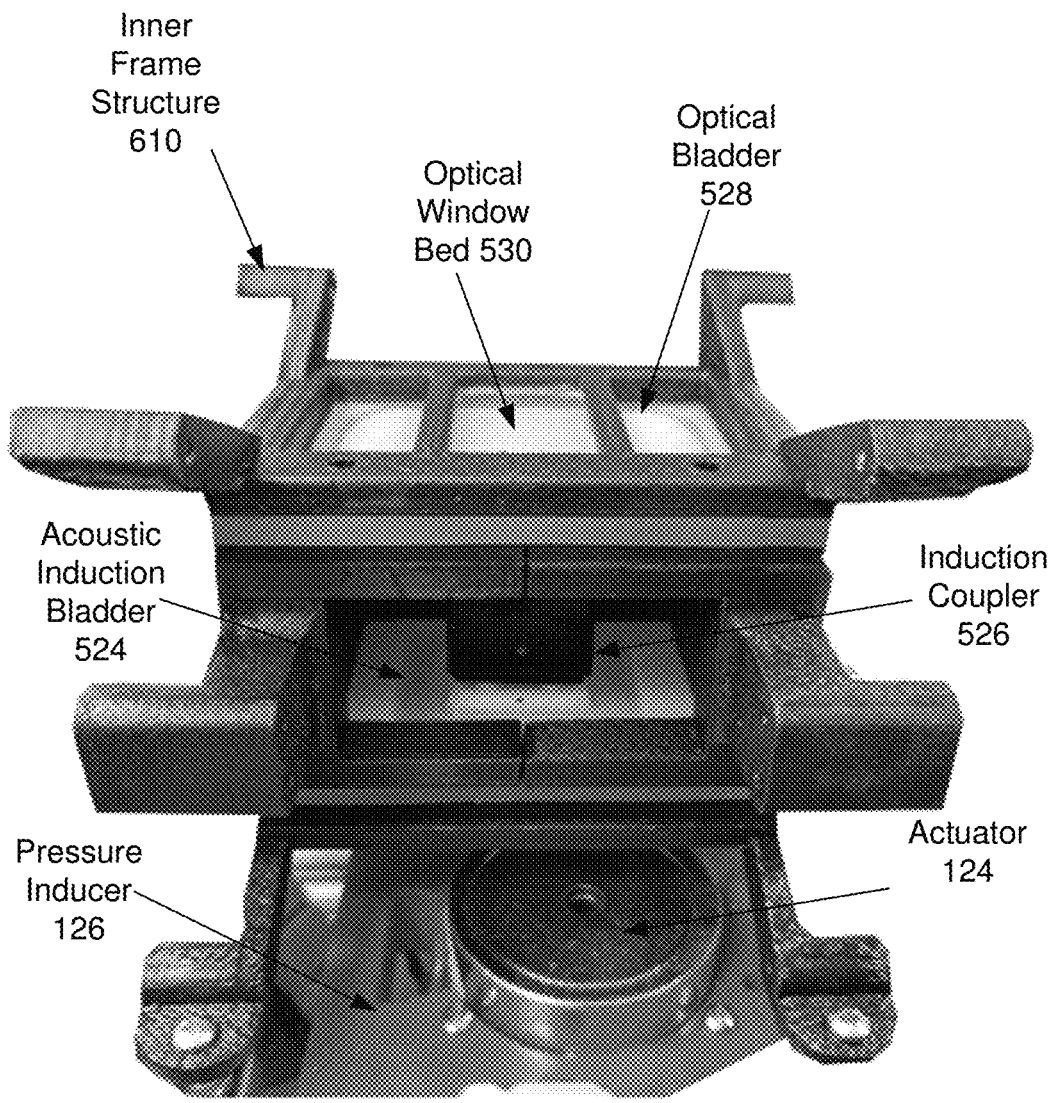
FIG. 6B illustrates another elevational view of an embodiment of the blood flow simulator with a pneumatic loop and a fluid loop.

FIG. 6B illustrates another elevational view of an embodiment of the blood flow simulator 100 with a pneumatic loop 500 and fluid loop 150. In this figure, the inner frame structure 610 is illustrated including the optical bladder 528 and acoustic induction bladder 524. The induction coupler 526 is coupled to the acoustic induction bladder 524. In one aspect, the induction coupler 526 is situated or configured to exert pressure onto a surface of the optical bladder 528 that is opposite or opposing to the surface of the optical window bed 530. Preferably, the induction coupler 526 is sized approximately to a size of the optical window bed 530. The induction coupler 526 is thus configured to generate a uniform force or pressure against the opposing surface of the optical window bed 530 of the acoustic induction bladder 524.

The inner frame structure 610 may also support one or more components of the pressure waveform generator 120. For example, the actuator 124 and pressure inducer may be supported by the inner frame structure 610 to decrease a size of the blood flow simulator 100.

Figure 7:
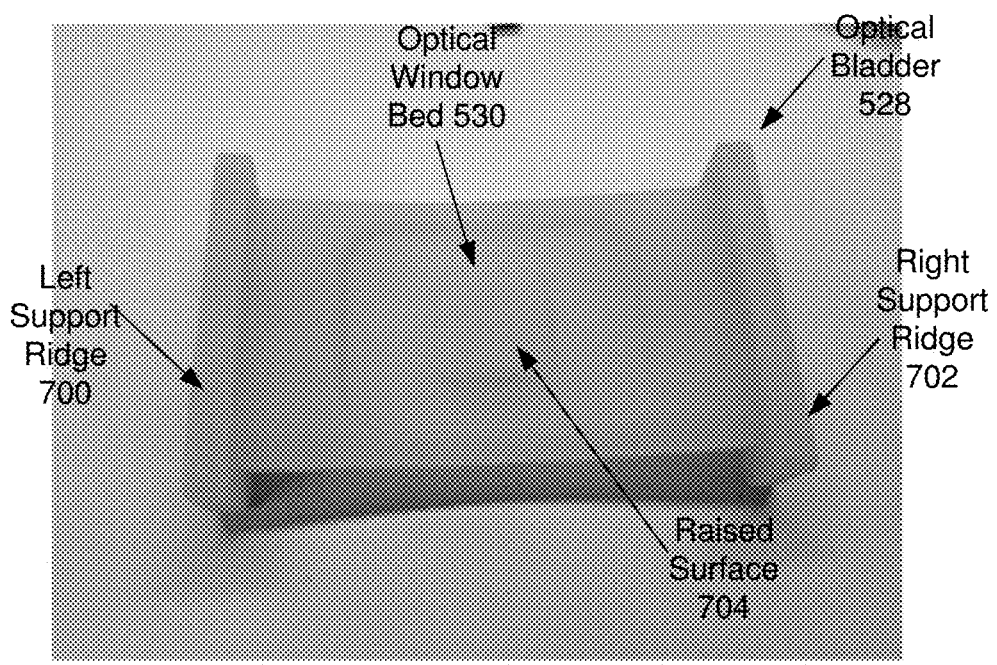
FIG. 7 illustrates an elevational view of an embodiment of the optical bladder including an optical window bed.

FIG. 7 illustrates an elevational view of an embodiment of the optical bladder 528 including an optical window bed 530. The optical bladder 528 includes a left support ridge 700 and right support ridge 702 configured for securing the optical bladder 528 within the inner frame structure 610. The optical window bed 530 may include a raised surface 704 formed to rise above a surface of the optical bladder 528. The raised surface 704 may induce formation of a bubble of air underneath between the fluid 152 and an opposing surface of the optical bladder 528.

The optical bladder 528 may comprise a flexible, elastic material such as silicon. The silicon material of the optical window bed 530 may include an elasticity that is approximately the same as or similar to arterial elasticity such that the optical window bed 530 has properties that react very similar to existing arterial beds located within a human body. The elastic properties of silicon are very well defined and so are the elastic properties of arteries. A mathematical model that maps the response of tissue to the response of the optical window bed is generated, and the silicon is manufactured to have a similar response to the mathematical model of tissue. The optical window bed 530 thus exhibits behavior similar to tissue. Though this embodiment is designed for reflective PPG configurations, the test site structure may be modified to simulate transmissive PPG configurations.

In addition, the silicon material of the optical window bed 530 may include optical properties that are similar or approximately the same as human tissue. One method for manufacturing material of the optical window bed 530 is described in the article, "Fabrication and characterization of silicone-based tissue phantoms with tunable optical properties in the visible and near infrared domain," by Frederick Ayers, Alex Grant, Danny Kuo, David J. Cuccia, and Anthony J. Durkin, Proc. of SPIE, Vol. 6870 (2008), which is hereby incorporated by reference herein. The article describes a fabrication process for Polydimethylsiloxane (PDMS) tissue simulating phantoms with tunable optical properties similar to human tissue to be used for optical system calibration and performance testing. The optical window bed 530 may thus include an optically engineered material that has similar scattering and absorption properties to tissue.

This manufacturing process may also include adding various skin tone dyes to the material of the optical window bed 530 to emulate various human skin tones or skin tones of other animals. Thus, different skin tones may be modeled. In addition, the optical properties of the optical window test bed 530 and the other material of the optical bladder 528 may be different. For example, the optical window test bed 530 may include material with different optical properties than other material of the optical bladder 528. The optical window test bed 530 may include material with similar optical properties to upper layers of skin while other material of the optical bladder 528 has elasticity similar to tissue. This difference more closely resembles the human body because the upper layers of skin have different scattering properties than the lower ones. The optical window bed 530 thus comprises material with elasticity and optical properties similar to human tissue.

The optical window bed 530 in one embodiment is a single enclosure surrounded by a very thin layer of silicon material. The single enclosure provides a uniform measuring surface for a sensor. The sensor may then measure a same amount of optical refraction over the whole area of the optical window bed 530. In another embodiment, the optical window bed 530 may include micro-channels that simulate vascular paths. For example, micro-channels with similar diameters to arteries found in humans or other patients may be implemented within the optical window bed 530. However, a sensor may detect variances in optical refraction across the optical window bed 530 depending on placement of the sensor with respect to a micro-channel or a micro-channel's walls. Other geometries of the optical window 530 may be implemented as well to simulate different tissue types or parts of a body.

Figure 8:
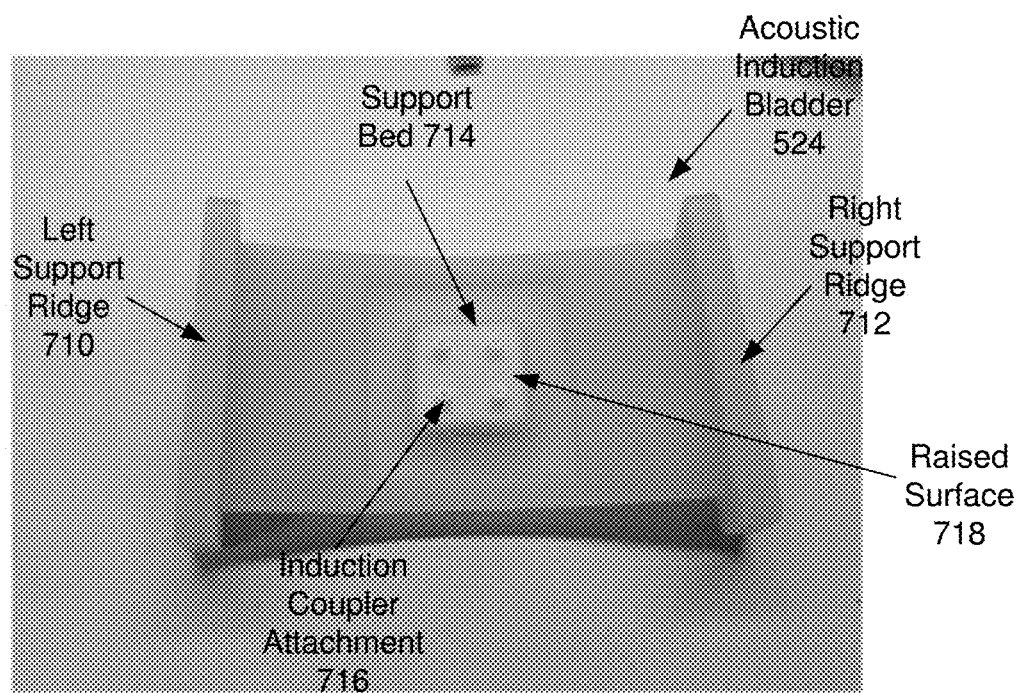
FIG. 8 illustrates an an elevational view of an embodiment of an acoustic induction bladder.

FIG. 8 illustrates an an elevational view of an embodiment of an acoustic induction bladder 524. The acoustic induction bladder 524 may comprise similar silicon material as the optical bladder 528. The acoustic induction bladder 524 similarly includes a left support ridge 710 and right support ridge 712 configured for securing the optical bladder 528 within the inner frame structure 610.

The acoustic induction bladder 524 may include a support bed 714. The support bed 714 includes one or more induction coupler attachments 716 configured to secure the induction coupler 526 to the support bed 714. The support bed 714 may include a raised surface 718 formed to rise above a surface of the acoustic induction bladder 524. The raised surface 718 in one aspect includes an area approximately same or similar to an area of the optical window bed 530. The support bed 714 and induction coupler 527 may thus exert a uniform pressure against the optical window bed 530.

Figure 9A:
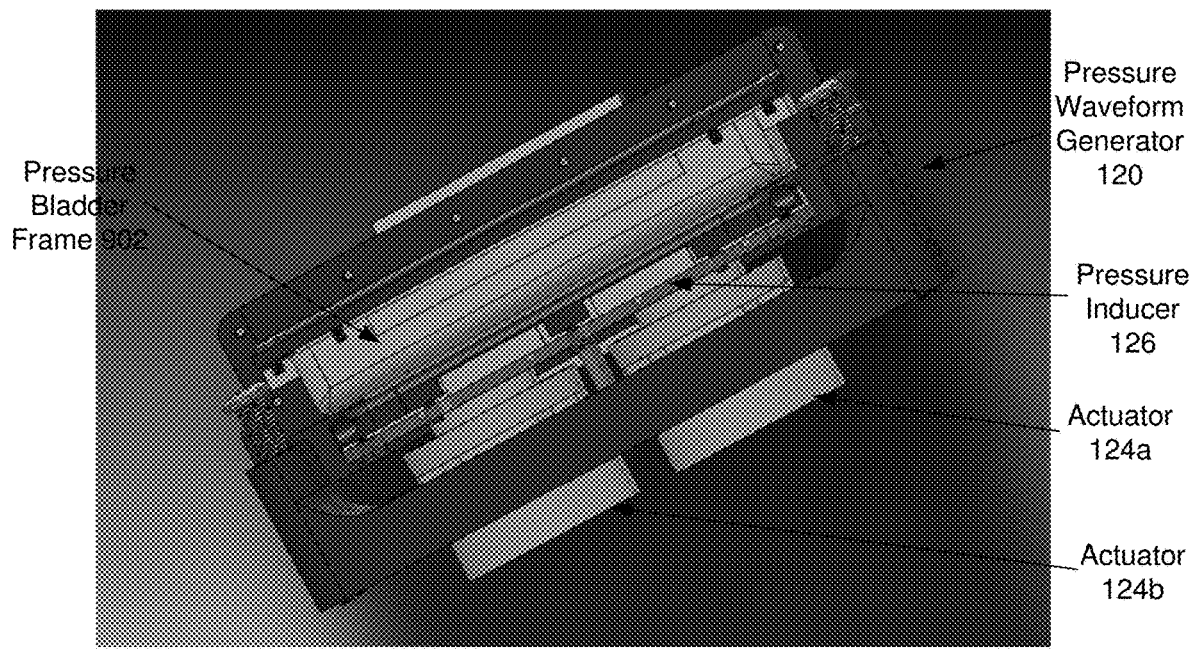
FIG. 9A illustrates an elevational front view of an embodiment of the pressure waveform generator.

FIG. 9A illustrates an elevational front view of an embodiment of the pressure waveform generator 120. In this embodiment, the pressure waveform generator 120 includes a pressure bladder 502 configured to hold pressurized gas 512. A pressure bladder frame 902 supports and holds the pressure bladder 502. The pressure bladder 502 comprises an elastic material with sufficient elasticity to exert pressure against the pressure inducer 126 in response to pressure waves in the gas 512. One or more actuators 124a, 124b,

124*c*, 124*d* exert pressure in parallel against the pressure inducer 126 in response to one of a plurality of pressure waveform files 112.

Figure 9B:
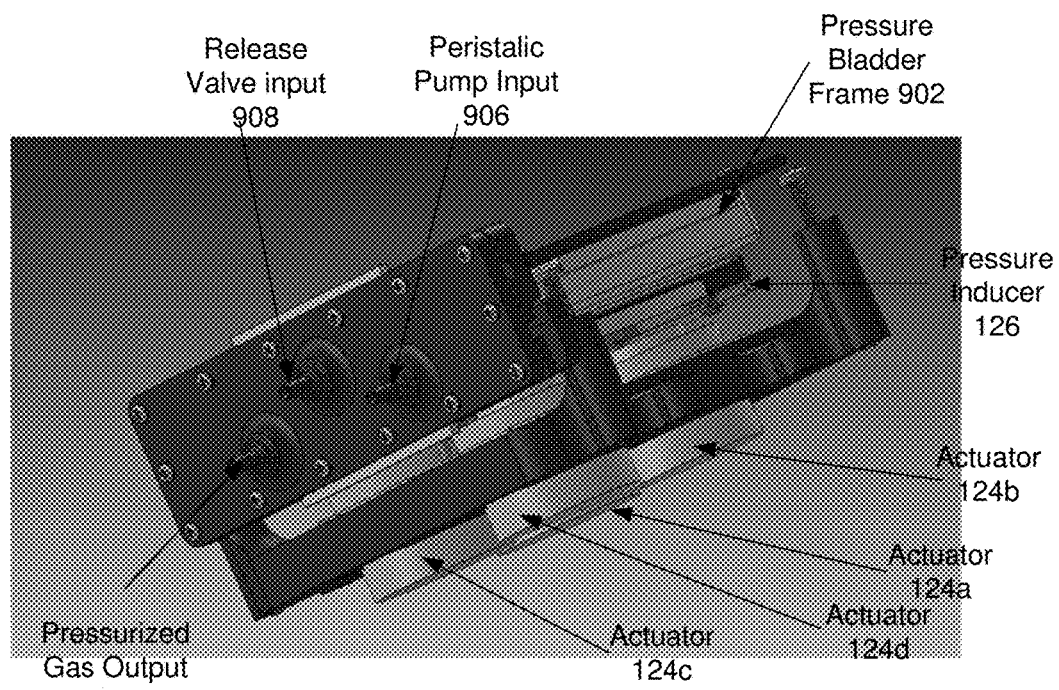
FIG. 9B illustrates an elevational back view of an embodiment of the pressure waveform generator.

FIG. 9B illustrates an elevational back view of an embodiment of the pressure waveform generator 120. The pressure waveform generator 120 includes a pump input 906 that receives pressurized gas 512 from a pump 170 or other source of pressurized gas. The pressurized gas 512 with induced waveforms is output to the acoustic induction bladder 524 from the pressurized gas output 904. The gas 512 may flow from the pressurized gas output 904 through the pneumatic pressurized tube 510 to the acoustic induction bladder 524. The pressure waveform generator 120 may also include a release valve input 908. The release valve input 908 may be coupled to a solenoid valve configured for release of the pressurized gas 512 upon completion of a trial. The pressure waveform generator 120 may be coupled to the inner frame structure 610 or outer frame structure 600 of the blood flow simulator 100 or may be a separate component of the blood flow simulator 100.

Embodiment-Pressure Waveform Files and Processing

Figure 10:
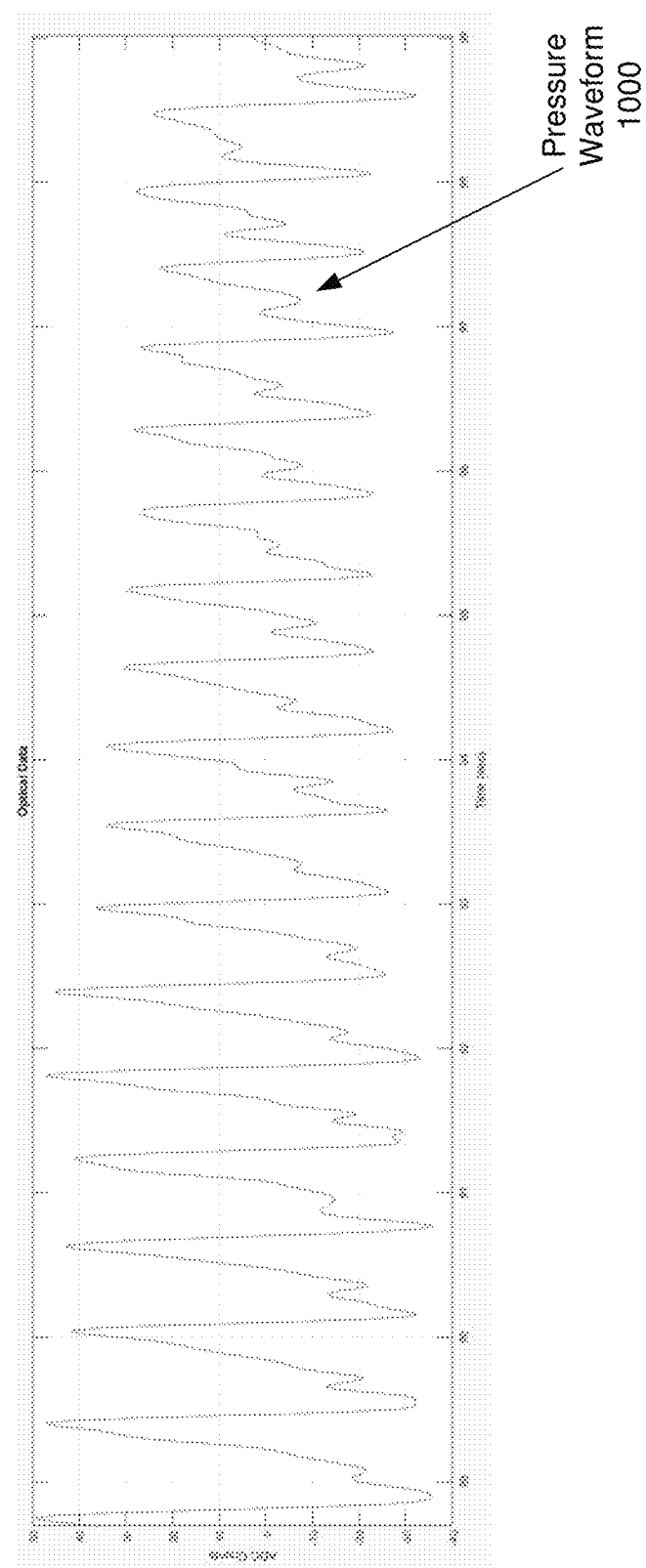
FIG. 10 illustrates a graphical schematic view of an embodiment of an exemplary pressure wave in a pressure waveform file.

FIG. 10 illustrates a graphical schematic view of an embodiment of an exemplary pressure waveform 1000 stored in one of the plurality of pressure waveform files 112. The pressure waveform 1000 in this example is an arterial pressure wave, e.g. the volumetric expansion and retraction of an artery as blood is pumped through the artery by the heart. This pressure waveform 1000 may be stored as one of the plurality of pressure waveform files 112. A user may select one of the pressure waveform files 112 to generate the pressure waveform 1000 in the fluid loop 150. Though this pressure waveform 112 is indicative of a normal cardiac rhythm, the plurality of pressure waveform files 112 may also include data indicative of arrhythmia, including at least one of: an accelerated heartrate, a low heart rate, or an irregular cardiac rhythm.

Figure 11A:
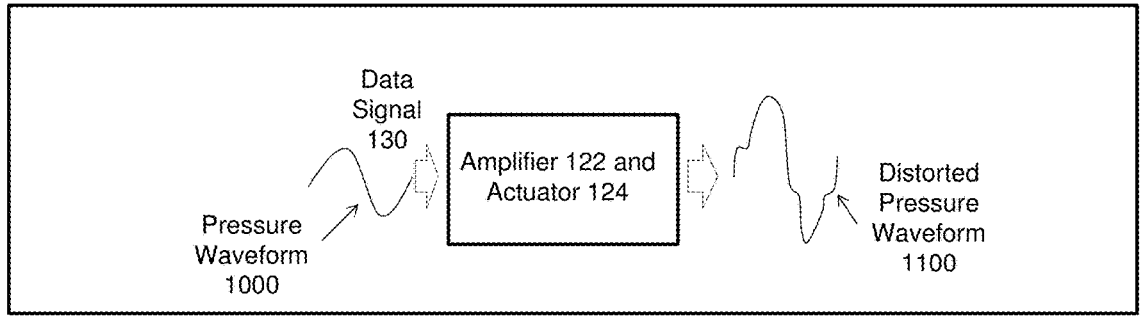
FIG. 11A illustrate a schematic block diagram of an embodiment of signal distortion in the blood flow simulator.

FIG. 11A illustrate a schematic block diagram of an embodiment of signal distortion in the blood flow simulator 100. A desired pressure waveform 1000 is input to the pressure waveform generator 120 as a data signal 130. The desired pressure waveform 1000 may be distorted by one or more components of the blood flow simulator 100, such as the amplifier 122 and actuator 124. The distorted pressure waveform 1100 is thus propagated through the blood flow simulator 100. For example, the amplifier 122 and one or more actuators 124 may generate a distorted pressure waveform 1100 in the fluid 152 in the fluid loop 150. To lower such distortion, the blood flow simulator 100 uses a feedback loop.

Figure 11B:
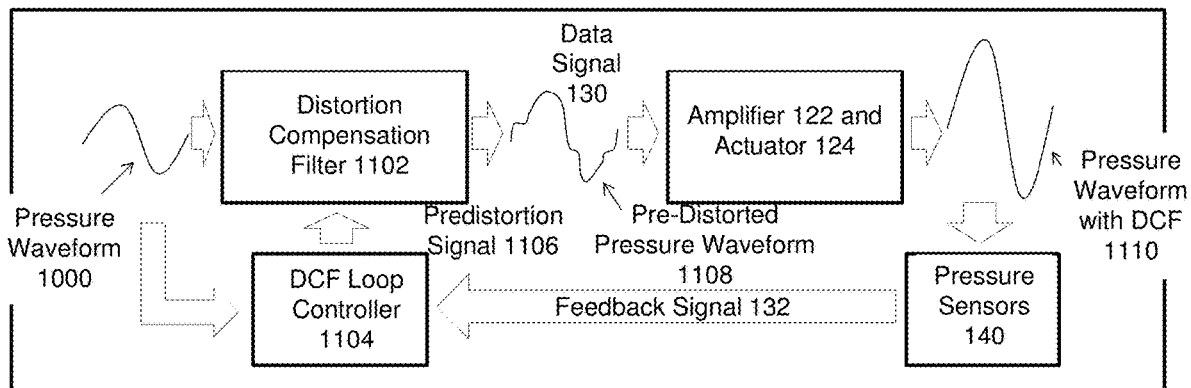
FIG. 11B illustrates a schematic block diagram of an embodiment of signal processing in response to the feedback loop by the blood flow simulator.

FIG. 11B illustrates a schematic block diagram of an embodiment of signal processing in response to the feedback loop by the blood flow simulator 100. The blood flow simulator 100 includes one or more pressure sensors 140 configured to measure the pressure waveform in the pneumatic loop 500 and fluid loop 150. The pressure sensors each generate a feedback signal 132 to a signal processor 106 in the system controller 110. The signal processor 106 includes, e.g. a distortion compensation filter (DCF) loop controller 1104 and distortion compensation filter 1102. The DCF loop controller 1104 receives the desired pressure waveform 1000 and plurality of feedback signals 132. The DCF loop controller 1104 determines a pre-distortion signal 1006 to apply to the pressure waveform 1000 to generate a pre-distorted pressure waveform 1108. The predistortion signal 1106 is computed to compensate for the distortion caused by the various components in the blood flow simulator 100. The pre-distorted pressure waveform 1108 is transmitted as the data signal 130 to the pressure waveform generator 120. The various components of the blood flow simulator 100, such as the amplifier 122 and actuator 124, thus output a pressure waveform with DCF 1110 that is more similar to the desired pressure waveform 1000. The pressure sensors 140 continue to monitor the pressure waveform 1000 in the blood flow simulator 100 to control the distortion or other anomalies.

Figure 12:
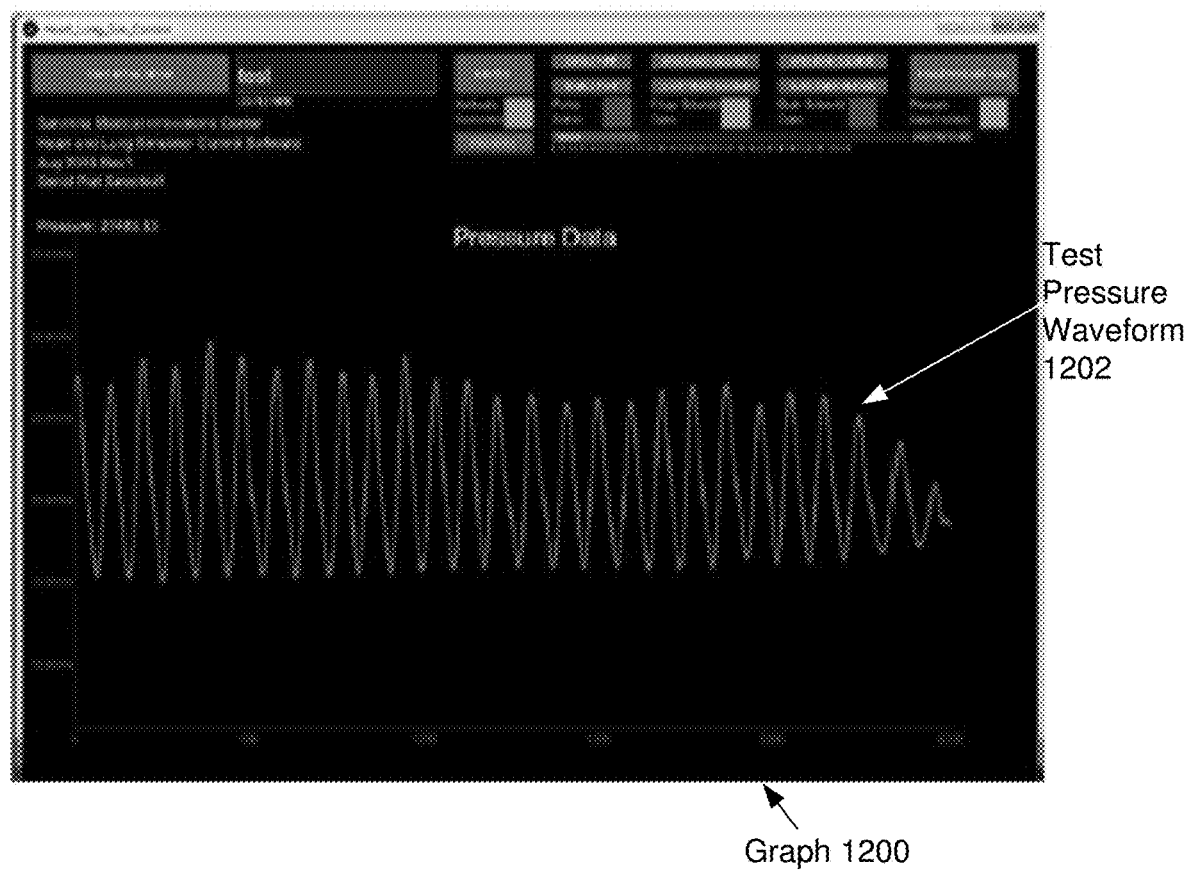
FIG. 12 illustrates a graphical schematic view of an embodiment of an exemplary test pressure waveform from a test sensor.

FIG. 12 illustrates a graphical schematic view of an embodiment of an exemplary test pressure waveform 1202 from a test sensor 550. The test sensor 550 in this example included a PPG circuit. The test sensor 550 measured the test pressure waveform 1202 in the fluid 152 from the optical window bed 530. The graph 1200 illustrates the pressure waveform 1202 measured by the test sensor 550 in the fluid loop 540 during a trial of the blood flow simulator 100. In one embodiment, a user interface 102 of the system controller 110 includes a graphical user interface to display the measured pressure waveform 1202. As seen in the graph 1200, the optical window bed 530 is able to duplicate the pressure waveform in the pressure waveform file 112.

Embodiment-Method of Operation of the Blood Flow Simulator

Figure 13:
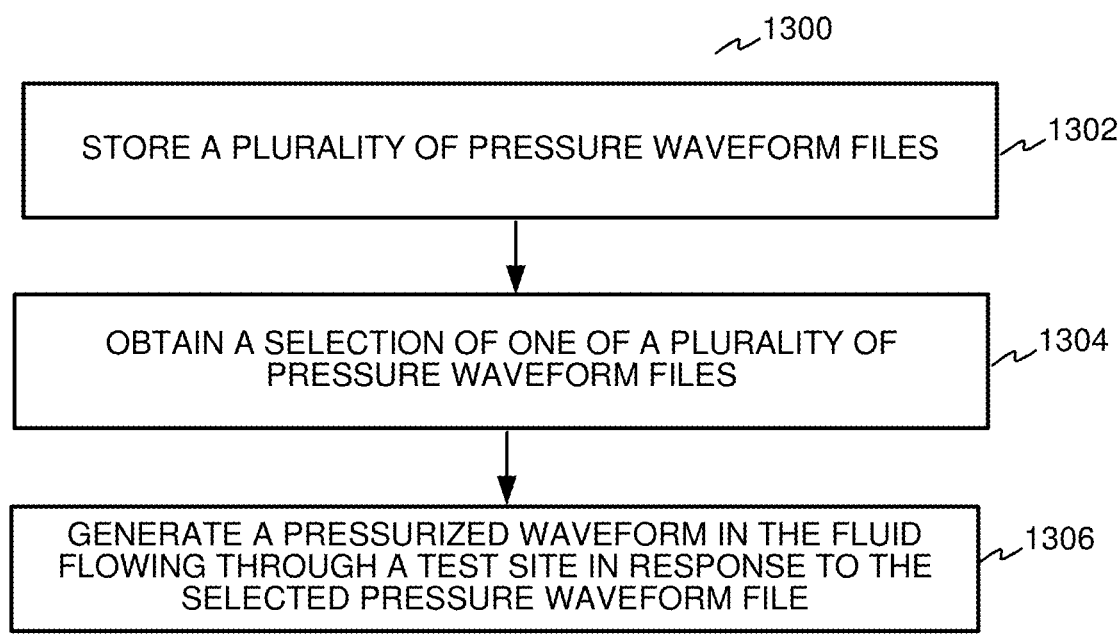
FIG. 13 illustrates a logical flow diagram of an embodiment of a method for a blood flow simulator.

FIG. 13 illustrates a logical flow diagram of an embodiment of a method 1300 for a blood flow simulator 100. The blood flow simulator 100 stores a plurality of pressure waveform files in the memory device of the system controller 110 at 1302. The pressure waveform files 112 include data from at least one of: a heart rate, a heartbeat waveform, an arterial blood pressure waveform, a respiration waveform, a background tissue response waveform, or a venous blood pressure waveform. In another aspect, the pressure waveform files 112 may also include data indicative of a heart rate, a heartbeat waveform, an arterial blood pressure waveform, a respiration waveform, a background tissue response waveform, or a venous blood pressure waveform. For example, the pressure waveform files 112 may include data indicative of arrhythmia, such as an abnormally slow or fast heart rate or an irregular cardiac rhythm.

The blood flow simulator 100 receives a selection of at least one of a plurality of pressure waveform files by the system controller 110, e.g. through a GUI or other user interface 102 at 1304. For example, to select the pressure waveform file 112, a user interface 102 may include a graphical user interface (GUI) that includes one or more settings or icons or pull down menus for a user to select one of the plurality of pressure waveform files 112. The blood flow simulator 100 generates a pressure waveform by a pressure waveform generator in test fluid flowing through a test site in response to the selected one of the plurality of pressure waveform files at 1306. The blood flow simulator 100 may thus simulate blood flow from a normal cardiac rhythm or simulate flood flow from an abnormal cardiac rhythm, such as an abnormally slow or fast heart rate or an irregular cardiac rhythm.

Figure 14:
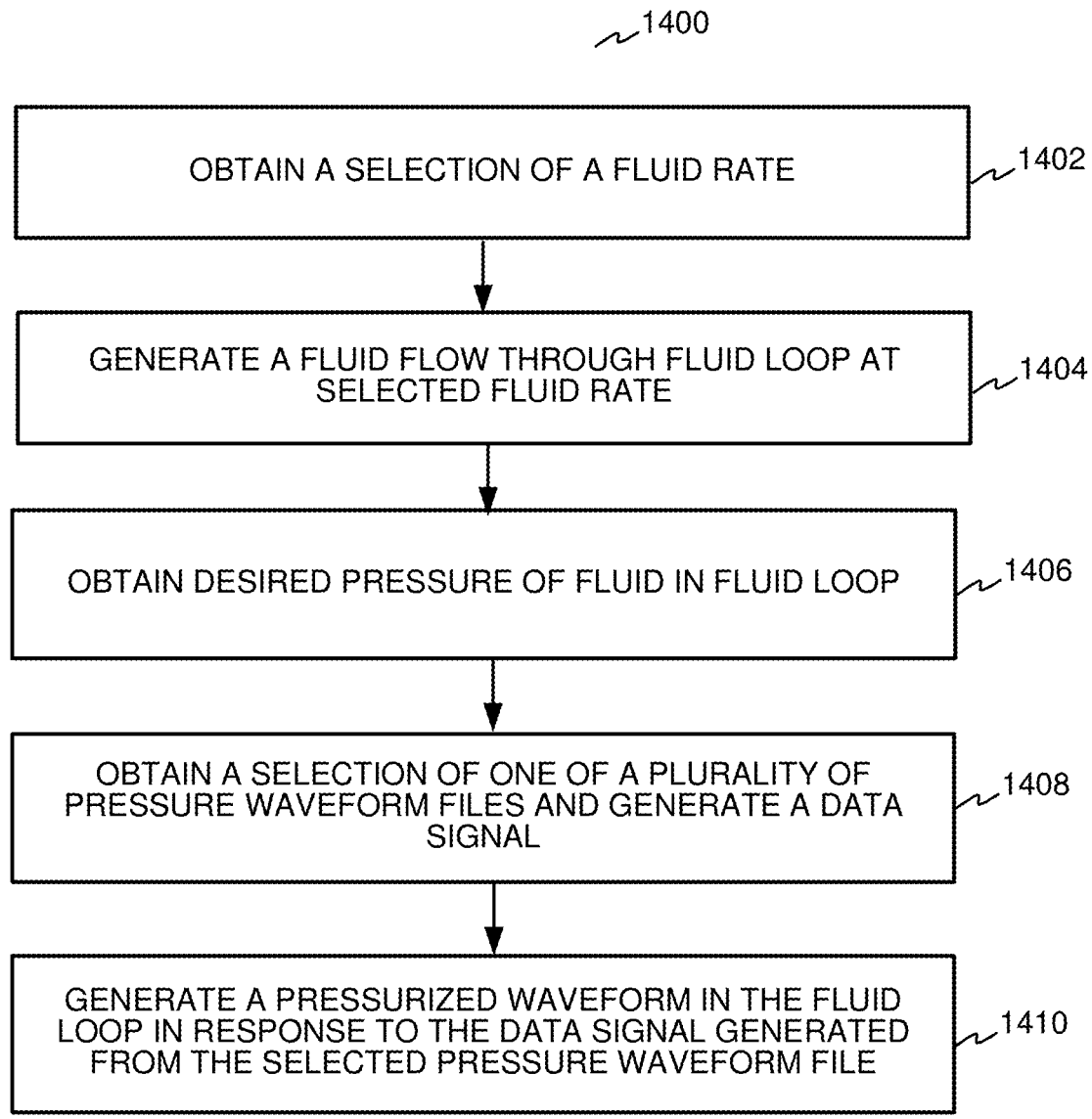
FIG. 14 illustrates a logical flow diagram of an embodiment of a method for a blood flow simulator in more detail.

FIG. 14 illustrates a logical flow diagram of an embodiment of a method 1400 for a blood flow simulator 100 in more detail. The blood flow simulator 100 obtains a selection of a fluid rate at 1402. For example, the user interface 102 may include a graphical user interface (GUI) that includes one or more settings or icons or menus for a user to select the fluid rate 1402. The system controller 110 is configured to control a pump 170*b* in the fluid loop 150 to generate a fluid flow at the selected fluid rate at 1404.

In one aspect, the pump 170*b* is activated for a duration until the fluid 152 obtains a desired pressure in the fluid loop 150, e.g., specifically in the optical bladder 528 at 1406. The blood flow simulator 100 then controls one or more valves 180b and 180c to close the fluid loop 150 to maintain the desired pressure. The pump 170 may then be deactivated. In another aspect, the pump 170b may continue to pump the fluid 152 through the fluid loop 150 at a desired flow rate, and the valves 180b, 180c remain open for fluid flow through the optical bladder 528.

The blood flow simulator 100 obtains a selection of one of the plurality of pressure waveform files 112 and generates a data signal 130 using the pressure waveform file at 1408. For example, the blood flow simulator 100 may perform data signal processing, such as distortion compensation filtering and pre-distortion, to generate the data signal 130. The data signal 130 is transmitted to the pressure waveform generator 120 to generate a pressurized waveform in the fluid loop 150 at 1410. The pressurized fluid with the pressure waveform propagates through the fluid loop 150.

Embodiment-Measurement of Concentration Levels in Blood Flow Simulator

The fluid 152 in the fluid loop 150 may include de-ionized water, water doped or dyed with substances of interest, blood, blood components or other types of fluid. One or more target substances may be added to the fluid 152, e.g. through an IV injection valve 544 or other means. The fluid loop 150 is designed such that surfaces that mechanically interface with the fluid 152 are inert to many common chemicals and substances found within the human body or blood as well as many chemicals and substances used for cleaning the fluid loop 150. The closed fluid loop 150 thus allows for common chemicals or real blood to be used in the blood flow simulator 100. The closed fluid loop 150 also allows for the cleaning and sanitation of the blood flow simulator 100. The blood flow simulator 100 may thus include a fluid 152 including one or more known target substances in known concentrations. This ability allows researchers to test performance of a test sensor 550 or configure a test sensor 550 for non-invasive blood chemical analysis.

For example, one type of test sensor 550 includes a photoplethysmography (PPG) circuit configured to detect oxygen saturation (SaO2 or SpO2) levels in blood flow, as well as heart rate, respiration rate and blood pressure. In addition, the PPG circuit in the biosensor is configured to detect concentration levels or indicators of one or more substances in the blood flow. See, e.g. the biosensor that implements PPG techniques to determine concentration levels of substances described in U.S. Utility application Ser. No. 15/275,388 entitled, "System and Method for Health Monitoring using a Non-Invasive, Multi-Band Biosensor," filed Sep. 24, 2016, which is hereby expressly incorporated by reference herein.

To test performance or calibrate one or more coefficients of a test sensor 550 (such as an absorption coefficient or wavelength for detection of a target substance), the concentration level of the target substance in the blood flow must be obtained using a known method, such as extracting blood at predetermined intervals. This process may be time consuming, cost probative, dangerous, or painful to perform on a patient. In addition, other variables may affect the calibration of the test sensor 550. The blood flow simulator 100 may be used for performance testing, calibration or configuration of a test sensor 550 to reduce the size and risk of clinical trials needed to configure and validate a test sensor 550.

Figure 15:
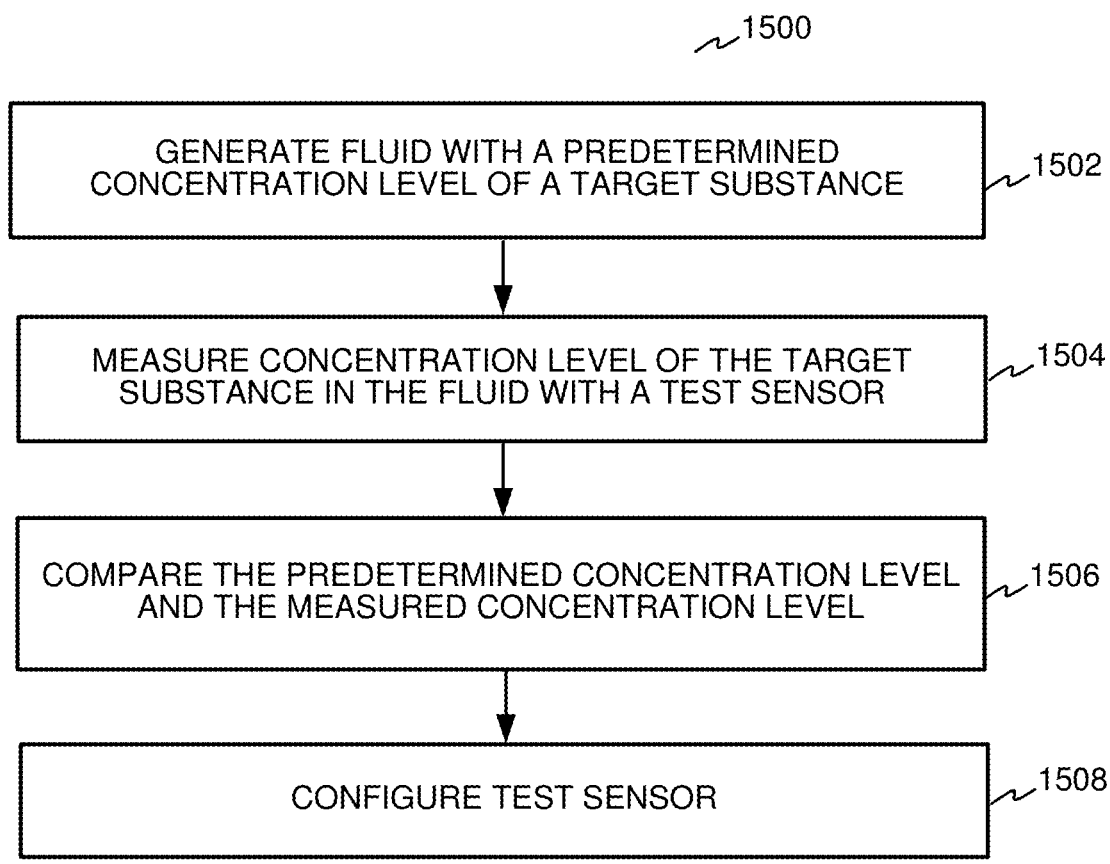
FIG. 15 illustrates a logical flow diagram of an exemplary method to measure concentration levels of a target substance in fluid of the blood flow simulator.

FIG. 15 illustrates a logical flow diagram of an exemplary method 1500 to measure concentration levels of a target substance in fluid 152 of the blood flow simulator 100. The measurements may be used, e.g. to configure a test sensor 550 or for performance testing of the test sensor 550. The fluid 152 in the fluid loop 150 is generated to include a predetermined concentration level of a target substance at 1502. The fluid 152 may be inserted within the blood flow simulator 100 already including the known concentration of the target substance or the target substance may be added through a port or IV injection valve 544 into the fluid loop 150.

The test sensor 550 then measures the concentration level of the target substance in the fluid 152 flowing through the fluid loop 150 in the blood flow simulator 100 at 1504. The measured concentration level is then compared with the predetermined concentration level of the target substance at 1506. The test sensor 550 may then be configured in response to the comparison at 1508. The predetermined concentration level of the target substance allows for a controlled testing environment for configuration and refinement of measurements by the test sensor 550.

For example, in use, the test sensor 550 uses a PPG circuit to emit light of a predetermined spectral composition and detect a response to the emitted light. The spectral response to the emitted light is analyzed, and the intensity of the detected light is determined. The intensity of the detected light is compared to the predetermined concentration level of the substance. The absorption coefficient for the substance may then be determined using Beer-Lambert equations or techniques. The above process may be repeated at one or more other frequencies. For example, the spectral analysis over a range or at multiple frequencies may be analyzed to determine one or more frequencies with a higher intensity or power level in response to the concentration level or presence of the target substance. Thus, one or more frequencies may be identified for detection of the target substance by the test sensor 550, and the absorption coefficient for the substance determined at the one or more frequencies.

In another embodiment, the blood flow simulator 100 may be used to generate a correlation table to determine the concentration level of a target substance by the test sensor 550. For example, in a calibration phase, a correlation table may be compiled through experimentation that includes R values or light intensity values I at one or more wavelengths $\lambda$ measured by the test sensor 550 when a corresponding predetermined concentration level for the substance was input in the blood flow simulator 100. In use, the test sensor 550 detects spectral responses and determines the R value or light intensity values I at one or more wavelengths $\lambda$ in a patient. The test sensor 550 then looks up the determined R value or detected light intensity values I in the correlation table to determine the concentration level of the substance.

In another embodiment, the skin tone of the simulated body part may be altered to determine calibration of the test sensor 550. For example, darker or lighter skin tones may be tested to determine any differences in measurements by the test sensor 550. The test sensor 550 may then be calibrated to account for different skin tones, e.g. by changing wavelengths, absorption coefficients, concentration level determinations, etc.

Figure 16:
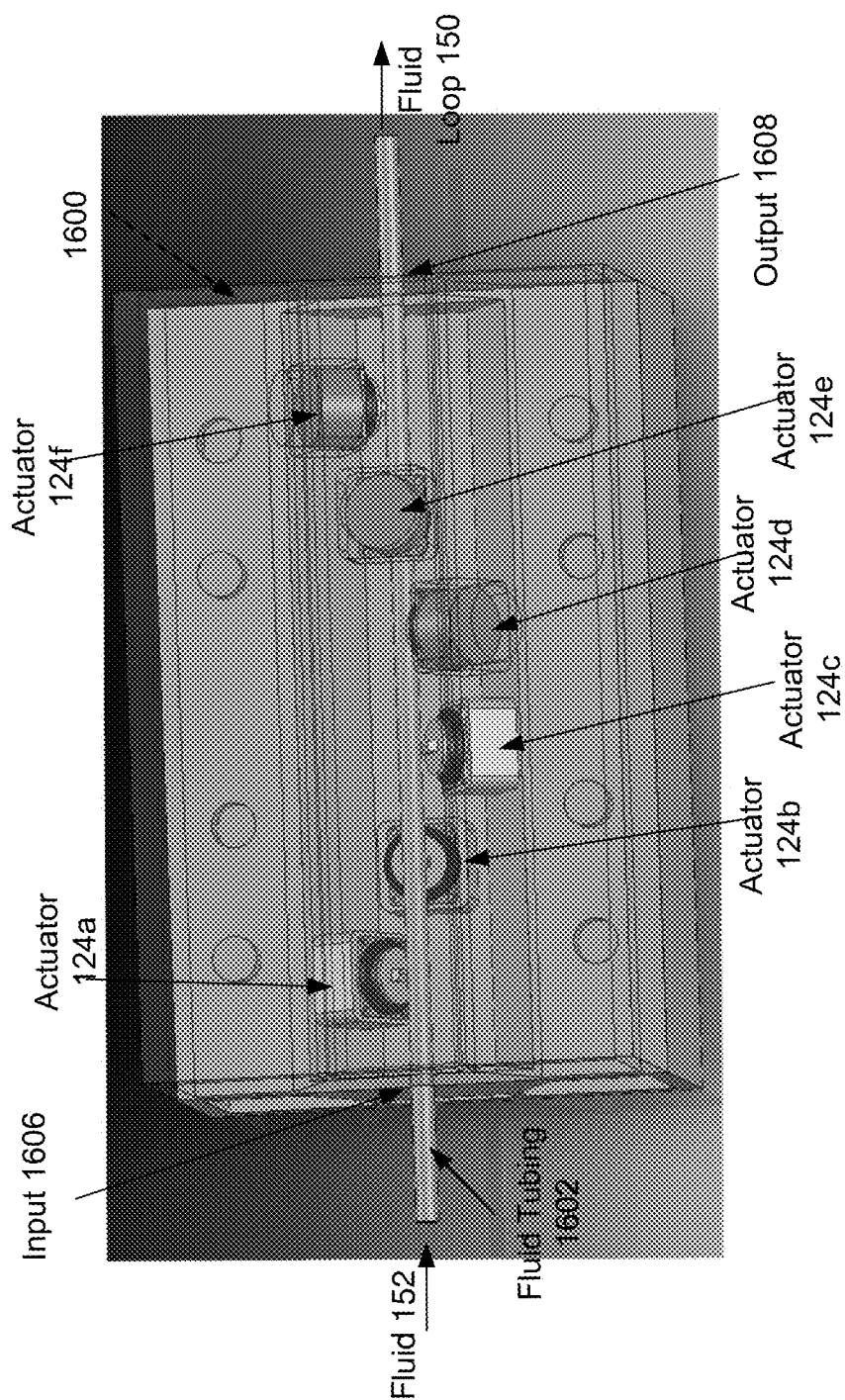
FIG. 16 illustrates an elevational view of another embodiment of the blood flow simulator with simulated spiral laminar flow.

FIG. 16 illustrates an elevational view of another embodiment of the blood flow simulator 100 with simulated spiral laminar flow. Spiral laminar flow has been shown to be the predominant blood flow pattern observed in a majority of patients in large arteries. To better replicate this natural blood flow pattern, the blood flow simulator 100 may include a spiral laminar flow (SLF) acoustic induction device 1600.

The SLF acoustic induction device 1600 includes a plurality of actuators 124 positioned along a length of flexible test fluid tubing with differing angles from the center of the fluid tubing 1602. For example, each of the plurality of actuators 124a, 124b, 124c, 124d, 124e, 124f are positioned equidistant with a 60 degree offset from adjacent actuators 124, for a total of 6 actuators each at a different 60 degree angle from the center of the fluid tubing 1602. In another embodiment, for example, four actuators 124 may be situated at a 90 degree offset from adjacent actuators 124. The plurality of actuators 124 may be equidistant or have differing distances from adjacent actuators 124.

In use, fluid 152 flows through the fluid tubing 1602 at an input 1606 of the SLF acoustic induction device 1600. The plurality of actuators 124a, 124b, 124c, 124d, 124e, 124f exert a pressure or force against the fluid tubing 1602 creating a spiral laminar blood flow pattern in the fluid 152. The fluid 152 flows through an output 1608 of the SLF acoustic induction device 1600 to a remainder of the fluid loop 150. The fluid loop 150 may include a testing surface for detection of the spiral laminar blood flow pattern.

In another embodiment, spiral laminar flow may be induced using different geometries of tubing. In one aspect, triangular or rectangular tubing may be implemented to mechanically induce spiral laminar flow in fluid in the tubing. For example, the triangular or rectangular tubing may be twisted or coiled or molded in that shape to induce a spiral laminar flow of the fluid. The fluid may then flow through a test site structure for testing by a medical device and/or connected in series to an oxygenator or respirator or similar device. Other applications may also be implemented in a simulator of spiral laminar flow as well. This technology may be used to induce the spiral laminar flow in between an output of a heart-lung machine into a catheter inserted in the body.

Figure 17:
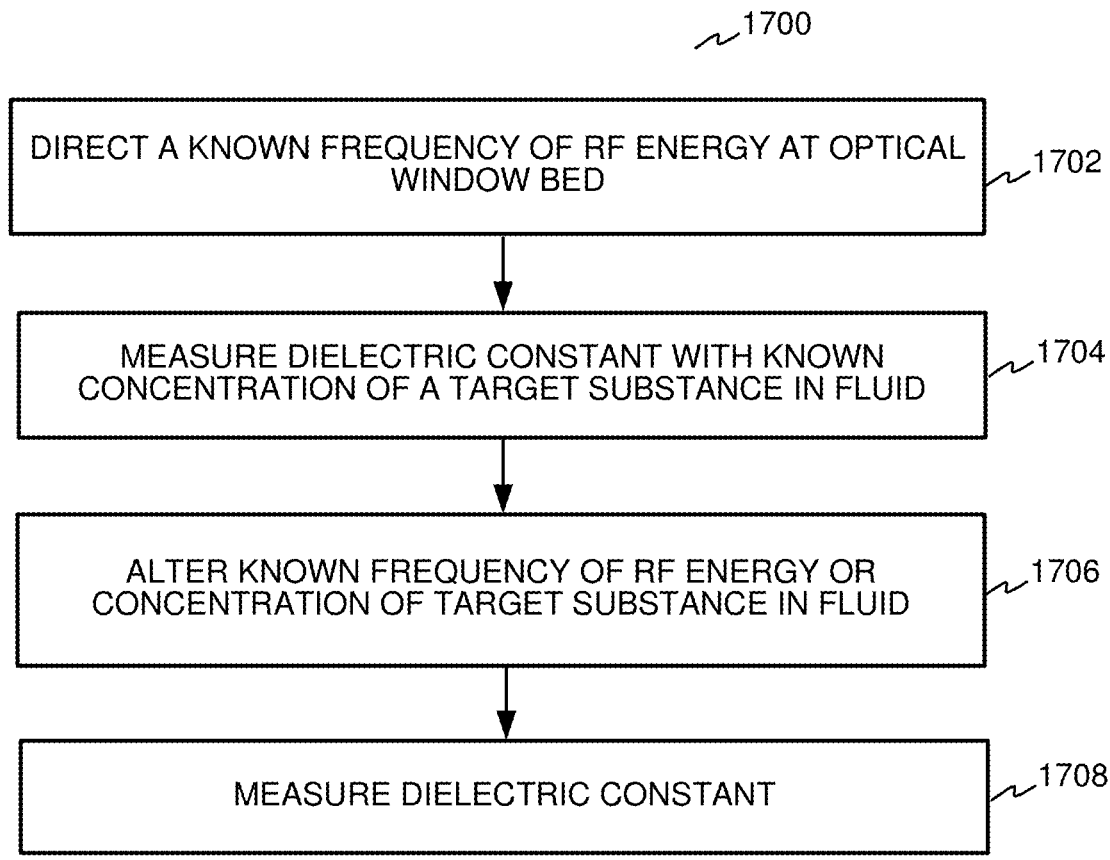
FIG. 17 illustrates a logical flow diagram of an exemplary method to measure dielectric constant of tissue by the blood flow simulator.

FIG. 17 illustrates a logical flow diagram of an exemplary method 1700 to measure dielectric constant of tissue by the blood flow simulator 100. The need for extensive data on the dielectric properties of human tissues is needed among researchers involved in the interactions of electromagnetic (EM) fields and biological systems. For example, the dielectric constant of human tissue decreases from $10^8$ to 1 for increasing EM frequencies from 1 Hz to 1 GHz. Generally, it is observed that the tissue permittivity decreases with frequency while tissue conductivity increases with frequency. The effects of the fluctuating dielectric constant are especially interesting when testing wearable devices. In another embodiment, fluctuating dielectric constant of human tissue has been shown to have biological causes, such as increased glucose levels. For example, glucose levels may be measured using RF sensors from the dielectric properties of tissue.

The blood flow simulator 100 may also be used to test the dielectric constant of tissue under various conditions. For example, a known frequency of RF energy may be directed at the optical window bed 530 or other test site of the blood flow simulator 100 at 1702. The dielectric constant is measured, e.g. using a fluid 152 with a known concentration of a target substance (such as glucose) at 1704. The known frequency of RF energy may be altered or the known concentration of the target substance at 1706. The dielectric constant is then measured again at 1708. The test sensor 550 may be configured using the results. The blood flow simulator 100 may thus be used to obtain data on the dielectric properties of human tissues.

The blood flow simulator 100 is thus configured to emulate blood flow through arteries or other blood vessels. The blood flow simulator 100 may thus be used for performance testing or configuration of medical devices.

In one or more aspects herein, a processor or processing circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory device includes a non-transitory memory device and may be an internal memory or an external memory and may be a single memory device or a plurality of memory devices. The memory device may include one or more of a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, components, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between components/devices and/or indirect connection between components/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects have been described with reference to specific examples. Various modifications and changes may be made, however, without departing from the scope of the embodiments as set forth in the claims. The specification and figures are illustrative, rather than restrictive, and modifications are intended to be included within the scope of the claims. Accordingly, the scope of the claims should be determined by the claims themselves and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of claims, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A blood flow simulator, comprising:
a system controller including a memory for storing a plurality of pressure waveform files;
a pressure waveform generator configured to generate a pressure waveform; and
an optical bladder including an optical window test bed, wherein the optical bladder is configured to induce the pressure waveform in fluid in the optical window test bed in response to at least one of the plurality of pressure waveform files;
an acoustic induction bladder, wherein the pressure waveform generator is configured to generate the pressure waveform in gas in the acoustic induction bladder in response to the at least one of the plurality of pressure waveform files; and
an induction coupler situated between the acoustic induction bladder and the optical bladder, wherein the induction coupler is configured to exert pressure onto the optical bladder in response to the pressure waveform in the gas in the acoustic induction bladder.

2. The blood flow simulator of claim 1, wherein the optical window test bed comprises a material with elasticity and optical properties similar to human tissue.

3. The blood flow simulator of claim 1, wherein the plurality of pressure waveform files includes data from at least one of: a heart rate, a heartbeat waveform, an arterial blood pressure waveform, a respiration waveform, a background tissue response waveform, or a venous blood pressure waveform.

4. The blood flow simulator of claim 1, wherein the plurality of pressure waveform files includes data indicative of arrhythmia, including at least one of: an accelerated heartrate, a low heart rate, or an irregular cardiac rhythm.

5. The blood flow simulator of claim 1, wherein the pressure waveform generator comprises:
a pressure bladder configured to hold gas;
an amplifier for amplifying data from at least one of the plurality of pressure waveform files to generate an amplified data signal; and
a pressure inducer configured to compress the pressure bladder in response to the amplified data signal to generate the pressure waveform in the gas.

6. The blood flow simulator of claim 5, wherein the pressure waveform generator further comprises:
at least one actuator configured to exert pressure on the pressure inducer in response to the amplified data signal.

7. The blood flow simulator of claim 6, wherein the at least one actuator includes at least one of: a piezoelectric actuator or an electromagnetic actuator.

8. The blood flow simulator of claim 1, further comprising:
an injection valve configured for injecting a target substance into the fluid to obtain a known concentration of the target substance in the fluid.

9. The blood flow simulator of claim 1, further comprising:
one or more pressure sensors configured to measure a pressure in the fluid and generate a feedback signal to the system controller.

10. The blood flow simulator of claim 9, wherein the system controller further includes:
a signal processor configured to receive the feedback signal from the one or more pressure sensors and generate a pre-distortion signal for a distortion compensation filter to obtain a data signal from the at least one of the pressure waveform files.

11. A method for simulating blood flow in a vessel, comprising:
processing by a system controller a selection of one of a plurality of pressure waveform files stored in a memory;

generating by a pressure waveform generator a pressure waveform in gas in an acoustic induction bladder using the selected one of the plurality of pressure waveform files; and inducing by an optical bladder the pressure waveform in fluid within an optical window test bed in the optical bladder; and exerting pressure by an induction coupler onto the optical bladder in response to the pressure waveform in the gas, wherein the induction coupler is situated between the acoustic induction bladder and the optical bladder.

12. The method of claim 11, wherein the optical window test bed comprises a material with elasticity and optical properties similar to human tissue.

13. The method of claim 12, wherein the plurality of pressure waveform files includes data from at least one of: a heart rate, a heartbeat waveform, an arterial blood pressure waveform, a respiration waveform, a background tissue response waveform, or a venous blood pressure waveform.

14. The method of claim 11, wherein the plurality of pressure waveform files includes data indicative of arrhythmia, including at least one of: an accelerated heartrate, a low heart rate, or an irregular cardiac rhythm.

15. The method of claim 11, further comprising:
amplifying data by an amplifier from the selected one of the plurality of pressure waveform files to generate an amplified data signal; and
compressing a pressure bladder using a pressure inducer in response to the amplified data signal to generate the pressure waveform in gas within the pressure bladder.

16. The method of claim 15, further comprising:
exerting pressure by at least one actuator on the pressure inducer in response to the amplified data signal.

17. The method of claim 16, wherein the at least one actuator includes at least one of: a piezoelectric actuator or an electromagnetic actuator.

18. The method of claim 11, further comprising:
injecting a target substance into the fluid to obtain a known concentration of the target substance in the fluid.

19. The method of claim 11, further comprising:
detecting a pressure in the fluid and generating a feedback signal to the system controller;
generating a pre-distortion signal for a distortion compensation filter to filter a data signal from the selected one of the pressure waveform files; and
generating by the pressure waveform generator the pressure waveform using the filtered data signal.

* * * * *